(12) United States Patent
Berenfeld et al.

(10) Patent No.: US 7,117,030 B2
(45) Date of Patent: Oct. 3, 2006

(54) METHOD AND ALGORITHM FOR SPATIALLY IDENTIFYING SOURCES OF CARDIAC FIBRILLATION

(75) Inventors: Omer Berenfeld, Dewitt, NY (US); Jose Jalife, Manlius, NY (US); Ravi Vaidyanathan, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 153 days.

(21) Appl. No.: 11/002,947

(22) Filed: Dec. 2, 2004

(65) Prior Publication Data
US 2006/0122526 A1   Jun. 8, 2006

(51) Int. Cl.
*A61B 5/0402* (2006.01)

(52) U.S. Cl. ........... 600/515; 600/512; 600/518; 600/523; 128/920; 607/4; 607/5

(58) Field of Classification Search ............ 607/4, 607/5; 600/512, 515, 518, 523; 128/920
See application file for complete search history.

(56) References Cited

U.S. PATENT DOCUMENTS

| | | | |
|---|---|---|---|
| 5,109,862 A | 5/1992 | Kelen et al. | |
| 5,549,109 A | 8/1996 | Samson et al. | |
| 5,578,007 A | 11/1996 | Imran | |
| 5,609,158 A | 3/1997 | Chan | |
| 5,676,153 A * | 10/1997 | Smith et al. | 600/515 |
| 5,782,899 A | 7/1998 | Imran | |
| 5,868,680 A * | 2/1999 | Steiner et al. | 600/518 |
| 6,622,042 B1 * | 9/2003 | Thacker | 607/14 |
| 2003/0069511 A1 * | 4/2003 | Stridh et al. | 600/515 |
| 2004/0176696 A1 * | 9/2004 | Mortara | 600/515 |
| 2004/0176697 A1 * | 9/2004 | Kappenberger et al. | 600/518 |
| 2004/0220489 A1 * | 11/2004 | Sherman et al. | 600/518 |

* cited by examiner

*Primary Examiner*—Robert E Pezzuto
*Assistant Examiner*—Deborah Malamud
(74) *Attorney, Agent, or Firm*—Sander Rabin

(57) ABSTRACT

A method and computer program product comprising an algorithm adapted to execute a method of identifying the spatial coordinates of a sustaining source of fibrillatory activity in a heart by computing a set of point-dependent dominant frequencies and a set of point-dependent regularity indices for a set of products of point-dependent unipolar discrete power spectra and point-dependent bipolar discrete power spectra, derived by spectral analyses of corresponding unipolar and bipolar cardiac depolarization signals simultaneously acquired from a set of points of the heart. A maximum dominant frequency is selected whose associated coordinates identify the point of the sustaining source of fibrillatory activity. The magnitude of the regularity index is interpreted to verify the identification of the spatial coordinates of the sustaining source of fibrillatory activity. When indicated, surgical intervention is directed to the spatial coordinates of the sustaining source of fibrillatory activity.

34 Claims, 7 Drawing Sheets

METHOD AND ALGORITHM FOR SPATIALLY IDENTIFYING SOURCES OF CARDIAC FIBRILLATION

FEDERAL GRANT

Some of the research described in this application was funded by Grant R01 HL60843 from the National Institutes of Health. The U.S. government may therefore have certain rights in the invention.

BACKGROUND OF THE INVENTION

1. Technical Field

The present invention generally relates to a method and algorithm for spatially identifying sources generative of cardiac fibrillation, and in particular, atrial fibrillation.

2. Related Art

2a. Atrial Fibrillation: Epidemiology, Incidence and Prevalence

Atrial fibrillation (AF) is the most frequently occurring sustained cardiac rhythm disturbance ("arrhythmia") in humans. AF may be intermittent or paroxysmal, or it may be a stable arrhythmia that may last for many years. One to two million Americans have chronic AF. Epidemiologic studies have shown that the prevalence and incidence of AF doubles with each advancing decade beyond 50 years of age. Although not usually considered a life-threatening arrhythmia, AF has been associated with a two-fold increase in total and cardiovascular mortality. Factors that may increase mortality in AF include age, mitral stenosis, aortic valve disease, coronary artery disease, hypertension, and congestive heart failure.

Clinically, AF is often categorized as:

[i] paroxysmal—generally characterized by predominant sinus rhythm with intermittent episodes of AF;
[ii] chronic—persistent or permanent AF;
[iii] acute—an episode of AF with an onset within 24 to 48 hours of diagnosis; and,
[iv] lone—variably defined, but generally considered to occur in the absence of cardiac disease.

The most clinically important consequences of AF are thromboembolic events and stroke. A four-fold to six-fold increased risk of stroke (15-fold in patients with a history of rheumatic heart disease) makes this arrhythmia one of the most potent risk factors for stroke in the elderly and the most common cause of cardiogenic stroke. The risk of stroke in nonvalvular AF varies with age and with the presence of concomitant cardiovascular disease and other risk factors for stroke. Most strokes associated with AF appear to be caused by cardiac emboli, presumably formed in fibrillating atria.

The presence of persistent rapid ventricular rates in association with AF may lead to impairment of ventricular function by a mechanism similar to that of tachycardia-mediated cardiomyopathy. This condition may be reversible. Improved ventricular function has been reported after complete atrioventricular (AV) node ablation, medical control of ventricular rate, or achievement of sinus rhythm. Evidence for development of atrial myopathy has also been reported in patients with AF in the absence of valvular disease. Mechanical and electrical cardiac remodeling could also promote further propensities toward AF and thromboembolism.

The most common underlying cardiovascular diseases associated with AF are hypertension and ischemic heart disease. Valvular heart disease, congestive heart failure, hypertension, and diabetes have been shown to be independent risk factors for AF. Other associated conditions include pulmonary embolism, thyrotoxicosis, chronic obstructive pulmonary disease, the Wolff-Parkinson-White syndrome, pericarditis, neoplastic disease, and the postoperative state. The cardiac rhythm of a normal heart may be precipitated into AF by excessive alcohol, stress, drugs, excessive caffeine, hypoxia, hypokalemia, hypoglycemia, and systemic infection.

Morbidity attributable to AF also includes limitation in functional capacity from symptoms of palpitations, fatigue, dyspnea, angina, or congestive heart failure.

2b. Normal Cardiac Electrophysiology

The heart is a blood pumping organ consisting of four chambers—two atria and two ventricles. The normal function of the heart depends on the periodic and synchronized contraction of the walls of its four chambers. The walls of the heart are comprised of millions of cells called cardiomyocytes, whose interiors are maintained at a transmembrane potential difference voltage of about 70 millivolts relative to the external environment; i.e., the cardiomyocytes are in a state of relative voltage polarization. The synchronized mechanical contraction of the walls of the heart's chambers is triggered by the sequential and coordinated depolarization of their cardiomyocytes. The measured aggregate manifestation this depolarization of the resting transmembrane potential difference in cardiomyocytes is called an action potential or depolarization impulse.

The normal propagation of every cardiac action potential starts spontaneously at a region of the heart's right atrium ("RA") known as the sino-atrial ("SA") node, from which the action potential spreads throughout both atrial walls, causing their synchronous contraction, and toward a region known as the atrio-ventricular ("AV") node. From AV node, the action potential propagates as a depolarization wave front into a specialized conduction system known as the His-Purkinje system, whose terminal branches conduct the action potential into the walls of the right and left ventricles.

The normal propagation of the action potential's wave front of depolarization in the walls the atria and the ventricles is relatively continuous and uninterrupted. The normal contraction of the heart accompanying the propagation of the depolarization wave front is called normal sinus rhythm ("NSR"). NSR depends on normal propagation of the action potential, which must always originate at the SA node, as opposed to some other ectopic focus of origin, and must always spread from the SA node precisely in the foregoing sequence of transmission to the AV node, and thence to and through the His-Purkinje conduction system.

2c. Electrophysiology of Atrial Fibrillation

Certain self-sustaining, irregular and non-physiologically sequential depolarization impulses ("arrhythmias") may arise from one or more ectopic (non-SA node—either pacemaker or reentrant) foci and either impair or eliminate the normal contracting rhythm of the heart, thereby impairing or destroying the heart's capacity to pump blood. Atrial fibrillation and ventricular fibrillation are two such arrhythmias.

During atrial fibrillation ("AF"), multiple depolarization wave fronts are generated in the atria, giving rise to vermiform atrial contractions responding to depolarization wave fronts that often have frequencies in excess of 400 cycles per minute. This rapid, disordered atrial activation results in loss of coordinated atrial contraction, with irregular electrical conduction to the AV node and His-Purkinje system, leading to sporadic ventricular contractions.

On the surface electrocardiogram ("ECG"), AF is characterized by the absence of visible discrete P waves or the presence of irregular fibrillatory waves, or both, and an irregular ventricular response.

Sustained AF depends on the uninterrupted aberrant periodic electrical activity of at least one discrete primary ectopic focus, hereinafter called a sustaining source of fibrillatory activity ("SSFA") that may behave as a reentrant circuit. The reentrant circuit is established by the interaction of propagating wave fronts of cardiac depolarization with either an anatomical or functional obstacles, i.e., tissue regions of variable refractoriness or excitability acting as intermittent conduction blocks, in a region of the heart, such as, for example the right atrium ("RA") or the right ventricle ("RV") in a process called "vortex shedding." These reentrant circuits act as sources ("mother rotors") that generate high-frequency depolarization wave fronts ("mother waves") emanating in rapid succession that propagate through both atria and interact with anatomic or functional obstacles acting as intermittent conduction blocks and maintaining the overall fibrillatory activity. Some of these anatomic or functional obstacles become secondary ectopic foci themselves generative of aberrant depolarization daughter wavelets having lower frequencies.

Some of these daughter wavelets may attenuate in amplitude and undergo decremental conduction. Others may be annihilated by collision with another daughter wavelet or a boundary; and, still others conduct circuitously to create new vortices of depolarization. The end result is the fragmentation or fractionation of the secondary depolarizing wave fronts emanating from these reentrant circuits into multiple independent daughter wavelets, giving rise to new wavelets, and so on—in a perpetual, globally aperiodic pattern that characterizes fibrillatory conduction.

Sustained AF is a function of several factors, including a nonuniform distribution reentrant circuits having relatively brief refractory periods over a sufficiently large area of cardiac tissue with the concomitant fractionation of a mother wave into a large number of independent daughter wavelets, possibly also having low conduction velocities.

2d. Atrial Fibrillation: Therapeutic Approaches

Radiofrequency ("RF") ablation of atrial tissue by application of energy through cardiac catheters has become a major therapeutic method for atrial fibrillation in patients. The RF ablation procedure consists of beneficially altering the electrical properties of cardiac tissue in the vicinity of the ablating catheter tip. The extent to which tissue is altered depends on the power and duration of the application, as well as on the characteristics of the tissue itself. For a typical RF ablation, a power of 20–40 Watts is delivered for 6–10 minutes to create an altered substrate in a cardiac volume with a radius of about 5 mm around the catheter tip.

The efficacy of RF ablation is suboptimal because of imprecise localization of tissue hosting the AF sources that are targeted. This situation prevails because methods for mapping sources of fibrillation rely on educated guesswork based upon subjective inferences from clinical electrophysiological data and vague identification criteria. Extensive ablation sufficient to modify cardiac tissues can cure many types of AF, but it exposes the patient to a higher risk of complications and to unacceptable fluoroscopy exposure times; on the other hand, more selective ablation that targets localized ectopic foci is safer, but may be less likely to effect a permanent cure of the AF, which may be become prone to recurrences. Accordingly, there is a need for improved targeting of RF ablation and other surgical interventions that seek to neutralize AF.

The present invention comprises an automated method for the detection and spatial identification of sources of fibrillation that is far more rapid and reliable than prevailing methods. Accordingly, the present invention may be expected to substantially reduce the duration of RF ablation and improve the success rate of the procedure by providing real-time spectrally guided RF ablation in patients.

SUMMARY OF THE INVENTION

The present invention provides a method of identifying the spatial coordinates of at least one sustaining source of fibrillatory activity ("SSFA") in a heart, and a computer program product, comprising a computer usable medium having a computer readable program code embodied therein, wherein the computer readable program code comprises an algorithm adapted to execute the method of identifying the spatial coordinates of at least one SSFA, the method comprising the steps of:

simultaneously acquiring a unipolar time-dependent depolarization signal and a corresponding bipolar time-dependent depolarization signal from each acquisition point of a set of acquisition points of the heart, each acquisition point having unique spatial coordinates;

forming a set of unipolar time-and-point-dependent depolarization signals by assigning to each unipolar time-dependent depolarization signal the spatial coordinates of the acquisition point from which it was acquired; and, forming a set of corresponding bipolar time-and-point-dependent depolarization signals by assigning to each corresponding bipolar time-dependent depolarization signal the spatial coordinates ($x_i$, $y_i$, $z_i$) of the acquisition point from which it was simultaneously acquired;

forming a set of unipolar point-dependent discrete power spectra by computing a unipolar point-dependent discrete power spectrum for each unipolar time-and-point-dependent depolarization signal; and, forming a set of bipolar point-dependent discrete power spectra by computing a bipolar point-dependent discrete power spectrum for each corresponding bipolar time-and-point-dependent depolarization signal;

forming a set of point-dependent discrete power spectrum products by multiplying each unipolar point-dependent discrete power spectrum by each corresponding bipolar point-dependent discrete power spectrum;

computing a point-dependent product dominant frequency for each point-dependent discrete product power spectrum, thereby forming a set of point-dependent product dominant frequencies;

selecting a maximum point-dependent product dominant frequency from the set of point-dependent product dominant frequencies;

assigning the spatial coordinates of the maximum point-dependent product dominant frequency to the SSFA.

The present invention advantageously provides a rapid, efficient, sensitive and specific computer implemented method for detecting identifying sources of cardiac fibrillation, thereby providing precision targeting for surgical intervention and termination of cardiac fibrillation.

DETAILED DESCRIPTION OF THE INVENTION

5a. The Heart and Fibrillation

Figure 1B:
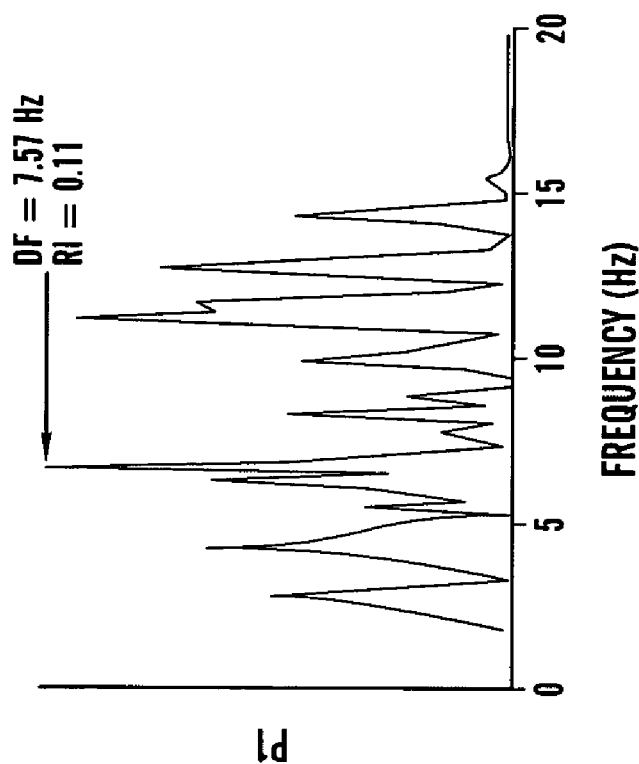
FIG. 1B shows a unipolar power spectrum corresponding to the exemplary unipolar electrogram of FIG. 1A.

As used herein, the term heart refers to a mammalian or human heart and includes but is not limited to its epicardial surfaces, endocardial surfaces, chambers, vessels, valves, nodes, conduction pathways, conduction bundles, muscles and allied structures.

As used herein, the term acquisition point refers to a point on or within the heart from which a unipolar and bipolar depolarization signal have been simultaneously acquired.

As used herein, the term fibrillation refers to all irregular rhythms of the heart having rates that are faster than the normal sinus rhythm rate of the heart, i.e., greater than about 40 beats per minute, including without limitation, atrial flutter, atrial fibrillation, ventricular flutter, ventricular fibrillation, monomorphic and polymorphic tachycardia, and torsade de point(s).

5b. Electrocardiogram

The electrical activity of the heart can be monitored because the action potential generated by a myocyte can be detected by devices that sense the electrical field changes it produces. The electrical activity of the heart is most commonly recorded and measured by use of a surface electrocardiogram ("ECG"), whose twelve electrodes ("leads") are applied to locations on the body's surface determined by long-established convention. The ECG leads independently measure and record twelve time-dependent macroscopic voltage changes at twelve orientations about the heart.

5c. Unipolar and Bipolar Time-Dependent Depolarization Signals

When more detailed information about the heart's electrical activity is necessary, a cardiac signal acquisition device may be disposed within the heart to acquire, i.e., to detect, measure, record and output as a signal, the heart's electrical activity from its endocardial surfaces. The electrical activity of the heart may also be acquired by a cardiac signal acquisition device from its epicardial surfaces or from within any of its tissues, such as, for example, from within its muscle tissue.

The cardiac signal acquisition device may function on the basis of electrical, optical, acoustic, or other signal acquisition and transduction methods, well known in the cardiac electrophysiological arts, whose time-dependent output is correlated with the electric depolarization of a cardiac myocyte; and, as used herein, is referred to as a time-dependent depolarization signal $S_i(t)$. A recorded time-dependent depolarization signal $S_i(t)$ is called an electrogram.

The cardiac signal acquisition devices used herein simultaneously acquire the heart's electrical activity in both unipolar and bipolar modes. For example, a cardiac signal acquisition device may comprise two electrodes, spaced about 1 mm apart, that simultaneously record the heart's electrical activity as a unipolar time-dependent depolarization signal $S_{UPi}(t)$ and a corresponding bipolar time-dependent depolarization signal $S_{BPi}(t)$, each describing the electrical activity at the contact points of the electrodes with an endocardial surface of the heart.

As described more fully infra., a time-dependent depolarization signal $S_i(t)$ derived from a point $P_i(x_i, y_i, z_i)$ on or within the heart may be associated with a point-dependent dominant frequency $DF_i(x_i, y_i, z_i)$ that may be identified from a point-dependent discrete power spectrum $DPS_i(f, x_i, y_i, z_i)$ derived from the time-dependent depolarization signal $S_i(t)$. A unipolar time-dependent depolarization signal $S_{UPi}(t)$ and a bipolar time-dependent depolarization signal $S_{BPi}(t)$ are combined in the present invention to improve the identification of the point-dependent dominant frequency $DF_i(x_i, y_i, z_i)$.

A bipolar time-dependent depolarization signal $S_{BPi}(t)$ removes far field electrical activity, but power contained in the high frequency range of its point-dependent discrete power spectrum $DPS_i(f, x_i, y_i, z_i)$ may exceed the power contained in the lower frequency range of the point-dependent discrete power spectrum $DPS_i(f, x_i, y_i, z_i)$ at which the heart is beating (i.e., the beating frequency). The power contained in the beating frequency range may be further degraded by the low signal-to-noise ratio that is typical of bipolar signals. While the power spectra of unipolar time-dependent depolarization signals contain less power in their high frequency ranges, unipolar signals may be significantly distorted by far-field electrical activity.

In view of the different spectral properties of unipolar and bipolar signals, the present invention advantageously multiplies their respective power spectra to enhance the power contained in a common band of local electrical excitation. Mathematically, the multiplication of a unipolar power spectrum by a bipolar power spectrum is equivalent to convolution of the unipolar and bipolar signals, which convolution results in the screening out of the uncommon distorting elements, such as harmonics and far-field effects.

Figure 1A:
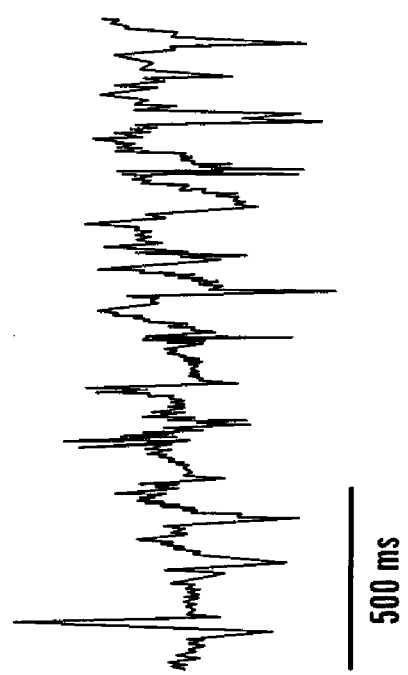
FIG. 1A shows an exemplary unipolar electrogram.

FIG. 1A shows an exemplary unipolar time-dependent depolarization signal acquired from an endocardial point; and, FIG. 1B shows an exemplary unipolar power spectrum corresponding to the exemplary unipolar time-dependent depolarization signal of FIG. 1A. The ordinate in FIG. 1A shows the relative amplitude of the exemplary unipolar time-dependent depolarization signal. The abscissa in FIG. 1A shows a scale marking 500 ms. The ordinate in FIG. 1B is labeled "P1," and indicates the power per unit frequency ("power density"). The abscissa in FIG. 1B is labeled "Frequency (Hz)."

Figure 2B:
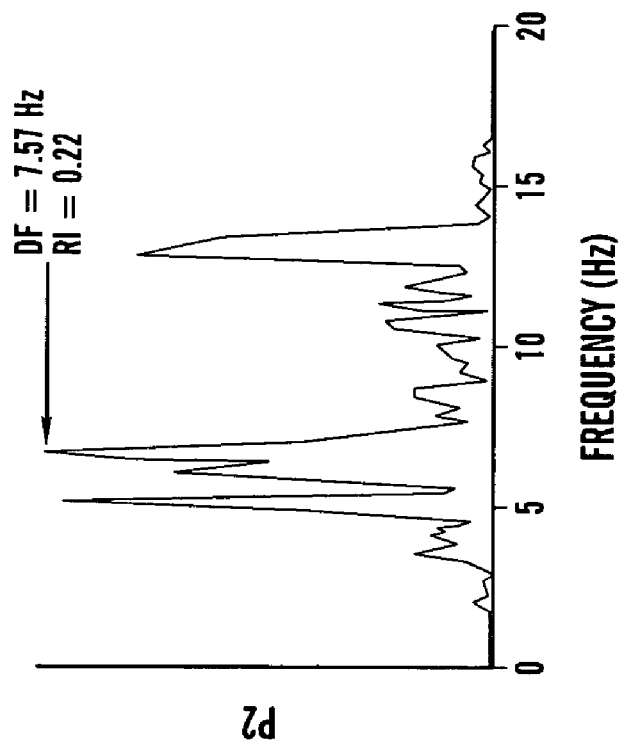
FIG. 2B shows a bipolar power spectrum corresponding to the exemplary bipolar electrogram of FIG. 2A.
Figure 2A:
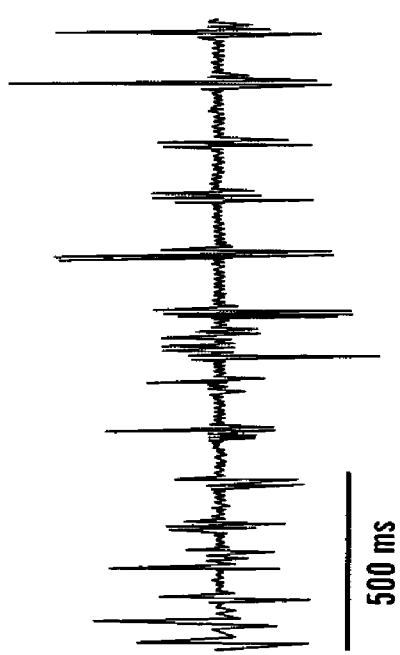
FIG. 2A shows an exemplary bipolar electrogram.

FIG. 2A shows an exemplary bipolar time-dependent depolarization signal acquired from the endocardial point of FIG. 1A; and, FIG. 2B shows an exemplary bipolar power spectrum corresponding to the time-dependent depolarization signal of FIG. 2A. The ordinate in FIG. 2A shows the relative amplitude of the exemplary bipolar time-dependent depolarization signal. The abscissa in FIG. 2A shows a scale marking 500 ms. The ordinate in FIG. 2B is labeled "P2," and indicates the power per unit frequency ("power density"). The abscissa in FIG. 2B is labeled "Frequency (Hz)."

In FIG. 1B and FIG. 2B, the frequency associated with the highest power density in both the unipolar power spectrum and the bipolar power spectrum—the "dominant frequency" DF—is identified at about 7.57 Hz. However, the degree to which the dominant frequency is the exclusive contributor to its associated time-dependent depolarization signal is influenced by the presence of other secondary frequencies at which significant power density peaks in both power spectra arise.

As more fully described infra., the level of certainty in the identification of the dominant frequency as the exclusive contributor to its associated time-dependent depolarization signal may be quantitated by computing a regularity index RI. The closer the regularity index RI is to 1, the greater the extent to which the dominant frequency is the exclusive contributor to its associated time-dependent depolarization signal. The closer the regularity index RI is to 0, the smaller the extent to which the dominant frequency is the exclusive contributor to its associated time-dependent depolarization signal. As shown in FIG. 1B, the RI of the unipolar power spectrum is about 0.11. As shown in FIG. 2B, the RI of the bipolar power spectrum is about 0.22.

Figure 3:
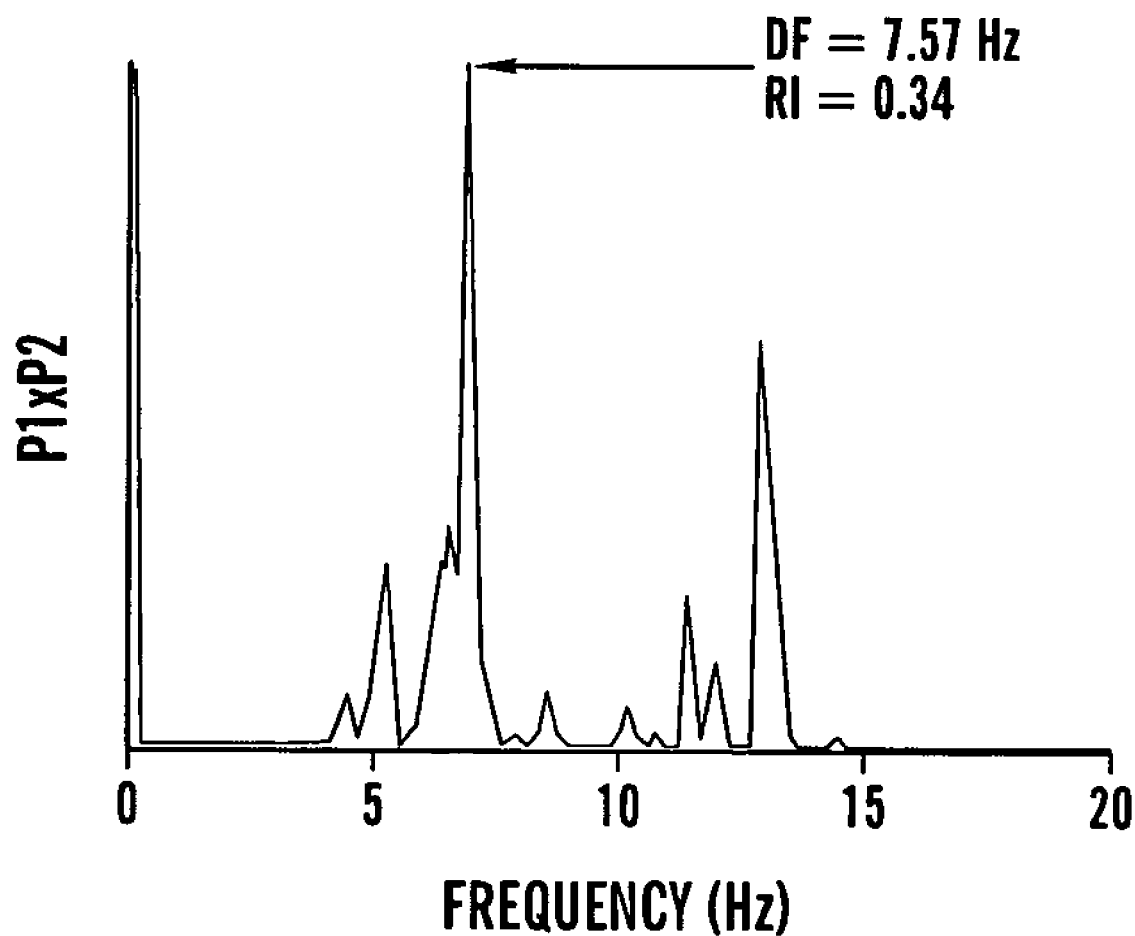
FIG. 3 shows the power spectrum product obtained from the multiplication of the unipolar power spectrum shown in FIG. 1B with the bipolar power spectrum shown in FIG. 2B.

FIG. 3 shows the power spectrum product obtained from the multiplication of the exemplary unipolar power spectrum shown in FIG. 1B by the exemplary bipolar power spectrum shown in FIG. 2B. The ordinate in FIG. 3 is labeled "P1×P2," and indicates the power per unit frequency ("power density"). The abscissa in FIG. 2B is labeled "Frequency (Hz)."

FIG. 3 shows that the power spectrum product obtained by multiplying the unipolar power spectrum by the bipolar power spectrum preserves the dominant frequency of about 7.57 Hz. However, relative to both the unipolar power spectrum and the bipolar power spectrum, the number of secondary power peaks in the power spectrum product is reduced together with the amplitudes of the secondary power peaks.

The reduction in the number and amplitude of secondary peaks obtained by multiplying a unipolar power spectrum from an endocardial point by its corresponding bipolar power spectrum from the same endocardial point has the advantageous effect of making the identification of the dominant frequency easier, and increasing level of certainty in the identification of the dominant frequency as the exclusive contributor to its associated time-dependent depolarization signal. This is indicated in FIG. 3 by the increase in the regularity index RI of over 50% to a value of about 0.34.

5d. "Roving" Signal Acquisition Mode

The method for identifying the spatial coordinates of sustaining sources of fibrillatory activity and the algorithm adapted execute the method (hereinafter "SSFA Identification Method and Algorithm") described herein, assigns to a time-dependent depolarization signal $S_i(t)$ the coordinates of a point $P_i(x_i, y_i, z_i)$ on or within the heart from which the time-dependent depolarization signal $S_i(t)$ is acquired by a cardiac signal acquisition device, thereby forming a point-and-time-dependent depolarization signal $S_i(t, x_i, y_i, z_i)$.

In the present invention, a "roving" cardiac signal acquisition device is used to sequentially probe a relatively inaccessible cardiac region, such as, for example, the atria, acquiring a time-dependent depolarization signal $S_i(t)$ from one location before being directed to another location. In a patient with fibrillation, the roving cardiac signal acquisition device may, for example, be used to record real-time episodes of atrial fibrillation over an acquisition time T of, for example of 5 seconds.

6. Spectral Analysis

Abnormalities in the form and propagation of a time-dependent depolarization $S_i(t)$ may be correlated with changes in its corresponding mathematical representation x(t). However, more useful information about an abnormal time-dependent depolarization signal $S_i(t)$ may be obtained from a study—a spectral analysis—of the mathematical properties of its frequency spectrum X(f). A spectral analysis is used in the present invention to compute a spatial identification within a coordinate system of the location of the electrophysiological source a fibrillating time-dependent depolarization signal $S_i(t)$. The identification of such a source, as described infra., provides a target for intervention and termination of the arrhythmia.

6a. Fourier Series

Generally, an integratable function of time having a period T, with a finite number of maxima and minima within T, and a finite number of discontinuities in T, can be represented as a Fourier series comprising a fundamental periodic function (sine or cosine) having a fundamental frequency and an infinite superposition of sine and cosine functions whose arguments are integer multiples of that fundamental frequency. These sine and cosine functions are called harmonics. A plot of the magnitudes of the amplitudes of these sines and cosines against their corresponding frequencies forms the frequency spectrum of the function of time.

6b. The Fourier Transform and the Frequency Spectrum

The Fourier transform is a generalization of the Fourier series applicable to aperiodic functions of time. The Fourier transform X(f) is a frequency domain representation of a function x(t) defined as:

$$X(f) = \int_{-\infty}^{\infty} x(t) e^{i2\pi ft} dt = F\{x(t)\} \tag{1}$$

The inverse Fourier transform is defined as:

$$x(t) = \int_{-\infty}^{\infty} X(f) e^{-i2\pi ft} df = F^{-1}\{X(f)\} \tag{2}$$

X(f) is called the frequency spectrum of x(t)

6c. The Power Spectrum

The power spectrum P(f) of x(t) is proportional to the energy per unit frequency interval of the frequency spectrum X(f) and is given by the product of X(f) with X(f)

$$P(f) = |X(f)|^2 = X(f) \cdot X(f) \tag{3}$$

6d. The Discrete Fourier Transform and the Fast Fourier Transform

Because a digital computer works only with discrete data, numerical computation of the Fourier transform of x(t), requires transformations of discretely sampled values of x(t) to yield a series of recorded values x(n). The equations which provide the digital analogues of the Fourier transform for discretely sampled data, such as, for example, a time-dependent depolarization signal $S_i(t)$, are called the discrete Fourier transform ("DFT"). A fast Fourier transform ("FFT") is a DFT algorithm.

A DFT is applied to a discretely sampled time-dependent depolarization signal $S_i(t)$, that is represented as a real-valued series that has N samples x(k) of the form $x_0$, $x_1$, $x_2$, ..., $x_k$, ..., $x_{N-1}$ where time at the kth sampling of $S_i(t)$ is $k\Delta t$, $\Delta t$ being the sampling interval in seconds. The DFT from the time domain t into the frequency domain f is then given by:

$$X(n) = \frac{1}{N}\sum_{k=0}^{N-1} x(k)\exp(-ik2\pi(n\Delta f)/N) \text{ for } n = 0, \ldots, N-1 \quad (4)$$

Where $n\Delta f$ is the frequency and $\Delta f$ is a fixed frequency interval, also known as the basic harmonic, or the frequency resolution. The frequency interval $\Delta f$ is related to the sampling interval $\Delta t$ and the number of samples N that are taken by $$\Delta f = 1/N\Delta t \quad (5)$$

6e. The Discrete Frequency Spectrum

X(n) is the discrete frequency spectrum of x(k). X(n) is complex, containing a real and an imaginary component; i.e., $$X(n) = X_{re}(n) + iX_{im}(n). \quad (6)$$

The discretely sampled $S_i(t)$ is acquired with a sampling rate $f_s$ over an acquisition time having a duration $$T = N\Delta t. \quad (7)$$

The sampling rates $f_s$ is related to the acquisition time T by $$f_s = N/T = 1/\Delta t \quad (8)$$

The frequency resolution $\Delta f$ is related to the sampling rater $f_s$ by $$\Delta f = 1/N\Delta t = 1/T = f_s/N \quad (9)$$

6f. The Discrete Power Spectrum

X(n) is commonly expressed as a discrete power spectrum P(n) that is proportional to the energy per unit frequency interval of the discrete frequency spectrum X(n), and is given by $$P(n) = X(n) \cdot X(n) \quad (10)$$

7. Spatial Identification of Sustaining Sources of Fibrillatory Activity

7a. Notation

The description of the SSFA Identification Method and Algorithm utilizes the notation scheme appearing in TABLE 1.

TABLE 1

NOMENCLATURE OF TERMS, ELEMENTS AND SETS

| Element or Term Symbol | Interpretation | Set Symbol |
|---|---|---|
| $cP_i(x_i, y_i, z_i)$ $cP_i$ | Cardiac points | $\{cP_i(x_i, y_i, z_i)\}$ $\{cP_i\}$ |
| $P_i(x_i, y_i, z_i)$ | Acquisition points | $\{P_i(x_i, y_i, z_i)\}$ |

TABLE 1-continued

NOMENCLATURE OF TERMS, ELEMENTS AND SETS

| Element or Term Symbol | Interpretation | Set Symbol |
|---|---|---|
| $P_i$ | | $\{P_i\}$ |
| $S_{UP}(t)$ | Time-dependent unipolar depolarization signal | |
| $S_{BP}(t)$ | Time-dependent bipolar depolarization signal | |
| $S_{UPi}$ $(t, x_i, y_i, z_i)$ | Time-and-point-dependent unipolar depolarization signal | $\{S_{UPi}(t, x_i, y_i, z_i)\}$ $\{S_{UPi}\}$ |
| $S_{BPi}$ $(t, x_i, y_i, z_i)$ | Time-and-point-dependent bipolar depolarization signal | $\{S_{BPi}(t, x_i, y_i, z_i)\}$ $\{S_{BPi}\}$ |
| $DFS_{UPi}$ $(f, x_i, y_i, z_i)$ $DFS_{UPi}$ | Point-dependent discrete unipolar frequency spectrum | |
| $DFS_{BPi}$ $(f, x_i, y_i, z_i)$ $DFS_{BPi}$ | Point-dependent discrete bipolar frequency spectrum | |
| $DPS_i$ $(f, x_i, y_i, z_i)$ $DPS_i$ | Point-dependent discrete power spectrum | $\{DPS_i(f, x_i, y_i, z_i)\}$ $\{DPS_i\}$ |
| $DPS_{UPi}$ $(f, x_i, y_i, z_i)$ $DPS_{UPi}$ | Point-dependent discrete unipolar power spectrum | $\{DPS_{UPi}(f, x_i, y_i, z_i)\}$ $\{DPS_{UPi}\}$ |
| $DPS_{BPi}$ $(f, x_i, y_i, z_i)$ $DPS_{BPi}$ | Point-dependent discrete bipolar power spectrum | $\{DPS_{BPi}(f, x_i, y_i, z_i)\}$ $\{DPS_{BPi}\}$ |
| $DPS_{PRODi}$ $(f, x_i, y_i, z_i)$ $DPS_{PRODi}$ | Point-dependent discrete power spectrum product | $\{DPS_{PRODi}(f, x_i, y_i, z_i)\}$ $\{DPS_{PRODi}\}$ |
| $DF_{UPi}$ $(x_i, y_i, z_i)$ $DF_{UPi}$ | Point-dependent unipolar dominant frequency | |
| $DF_{BPi}$ $(x_i, y_i, z_i)$ $DF_{BPi}$ | Point-dependent bipolar dominant frequency | |
| $DF_i$ $(x_i, y_i, z_i)$ $DF_i$ | Point-dependent dominant frequency | $\{DF_i(x_i, y_i, z_i)\}$ $\{DF_i\}$ |
| $DF_{PRODi}$ $(x_i, y_i, z_i)$ $DF_{PRODi}$ | Point-dependent product dominant frequency | $\{DF_{PRODi}(x_i, y_i, z_i)\}$ $\{DF_{PRODi}\}$ |
| $RI_i$ $(x_i, y_i, z_i)$ $RI_i$ | Point-dependent regularity index | $\{RI_i(x_i, y_i, z_i)\}$ $\{RI_i\}$ |
| $RI_{UPi}$ $(x_i, y_i, z_i)$ $RI_{UPi}$ | unipolar point-dependent regularity index | $\{RI_{UPi}(x_i, y_i, z_i)\}$ $\{RI_{UPi}\}$ |
| $RI_{BPi}$ $(x_i, y_i, z_i)$ $RI_{Bpi}$ | bipolar point-dependent regularity index | $\{RI_{BPi}(x_i, y_i, z_i)\}$ $\{RI_{BPi}\}$ |
| $RI_{PRODi}$ $(x_i, y_i, z_i)$ $RI_{PRODi}$ | Point-dependent product regularity index | $\{RI_{PRODi}(x_i, y_i, z_i)\}$ $\{RI_{PRODi}\}$ |
| $DF_{MAXi}$ $(x_i, y_i, z_i)$ | Maximum point-dependent dominant frequency | |
| $DF_{MAXPRODi}$ $(x_i, y_i, z_i)$ | Maximum point-dependent product dominant frequency | |
| $\Delta f_i$ | Frequency resolution | |
| $\Delta_i DF$ | Dominant frequency band | |
| $F_{lim1}$ | First frequency limit | |
| $F_{lim2}$ | Second frequency limit | |
| $F_{lim3}$ | Third frequency limit | |
| $F_{lim4}$ | Fourth frequency limit | |

7b. Dominant Frequency

Figure 4A:
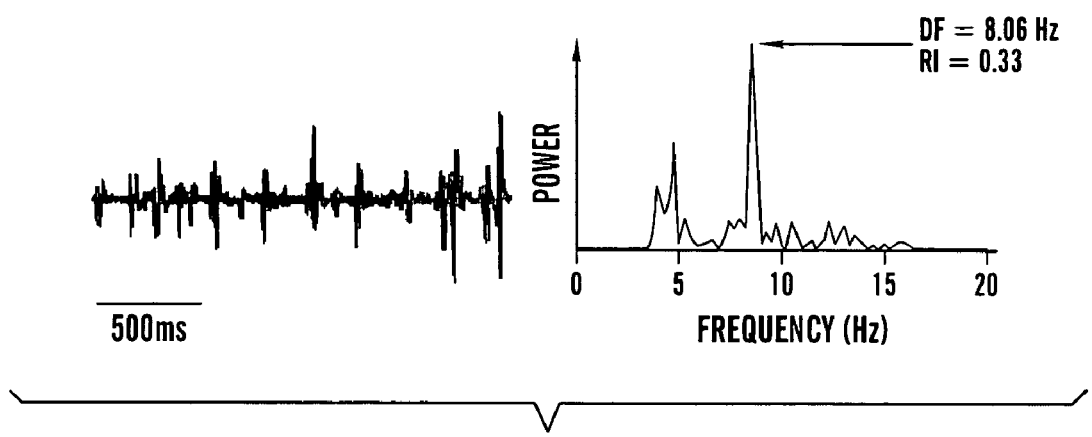
FIG. 4A–4C shows graphs of three exemplary point-and-time-dependent depolarization signals and corresponding graphs of point-dependent discrete power spectra.
Figure 4B:
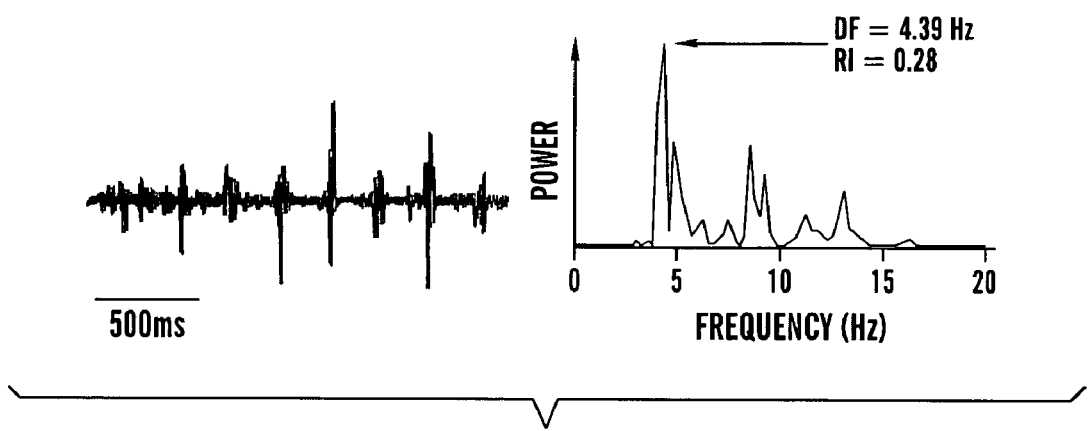
Figure 4C:
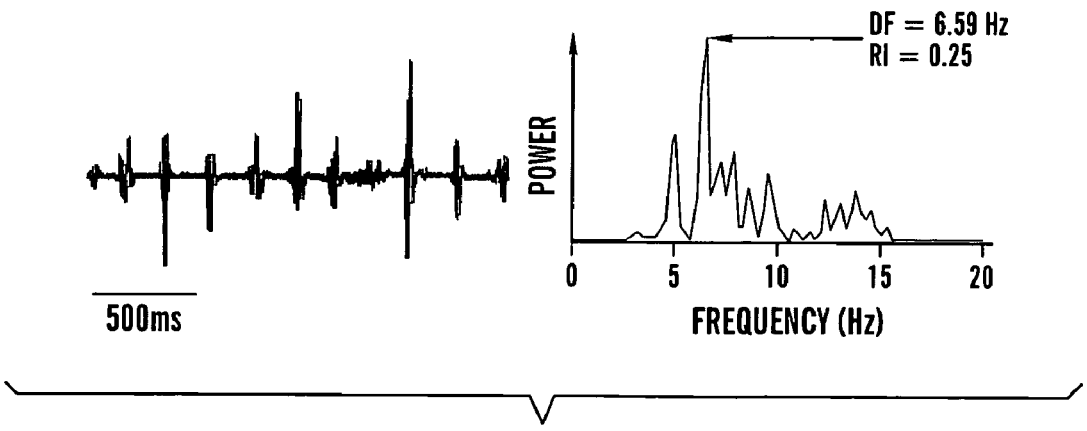

FIG. 4 shows graphs of three exemplary point-and-time-dependent depolarization signals A, B and C acquired by a cardiac signal acquisition device from three different locations ("acquisition points") on the posterior endocardial wall of the left atrium of a patient with paroxysmal atrial fibrillation. For purposes of illustration, the graphs shown in FIG.

4 are intended to generically represent either unipolar or bipolar depolarization signals.

The ordinate of each graph shows the relative amplitude of an exemplary point-and-time-dependent depolarization signal $S_i(t, x_i, y_i, z_i)$ in volts and the abscissa of each graph shows time (relative to a scale bar of 500 ms). To the left of each graph of each exemplary point-and-time-dependent depolarization signal there is shown a graph of its corresponding point-dependent discrete power spectrum $DPS_i(f, x_i, y_i, z_i)$ or $DPS_i$ The ordinate of each graph of a discrete power spectrum shows the power per unit frequency ("power density"). The abscissa of each power spectrum graph shows frequency in Hz.

As shown in FIG. 4, during an episode of fibrillation, a discrete point-dependent power spectrum $DPS_i(f, x_i, y_i, z_i)$ computed from a time-and-point-dependent depolarization signal $S_i(t, x_i, y_i, z_i)$, acquired from an acquisition point $P_i(x_i, y_i, z_i)$ on or within the heart, is characterized by a set of discrete peaks having bandwidths that are distributed across a frequency range of about 3 Hz to about 15 Hz.

The dominant frequency (designated in FIG. 4 by the letters "DF") is the frequency in the point-dependent discrete power spectrum $DPS_i (f, x_i, y_i, z_i)$, derived from a time-and-point-dependent depolarization signal $S_i (t, x_i, y_i, z_i)$ acquired from that acquisition point $P_i(x_i, y_i, z_i)$ on or within the heart that is associated with an absolute maximum power density, (i.e., maximum amplitude), in the point-dependent discrete power spectrum $DPS_i (f, x_i, y_i, z_i)$.

The SSFA Identification Method and Algorithm assigns to the dominant frequency the coordinates assigned to the time-and-point-dependent depolarization signal $S_i (t, x_i, y_i, z_i)$, from which it is derived, thereby forming a point-dependent dominant frequency $DF_i (x_i, y_i, z_i)$ or $DF_i$. The point-dependent dominant frequency $DF_i (x_i, y_i, z_i)$ is considered the activation frequency of its associated time-and-point-dependent depolarization signal $S_i (t, x_i, y_i, z_i)$.

The unipolar point-dependent dominant frequency $DF_{UPi} (x_i, y_i, z_i)$ of an acquisition point $P_i(x_i, y_i, z_i)$ on or within the heart is the frequency in the unipolar point-dependent discrete power spectrum $DPS_{UPi}(f, x_i, y_i, z_i)$, derived from a unipolar time-and-point-dependent depolarization signal $S_{UPi}(t, x_i, y_i, z_i)$ acquired from that acquisition point $P_i(x_i, y_i, z_i)$ on or within the heart that is associated with an absolute maximum power density in the unipolar point-dependent discrete power spectrum $DPS_{UPi} (f, x_i, y_i, z_i)$.

The bipolar point-dependent dominant frequency $DF_{BPi} (x_i, y_i, z_i)$ of an acquisition point $P_i(x_i, y_i, z_i)$ on or within the heart is the frequency in the bipolar point-dependent discrete power spectrum $DPS_{BPi}(f, x_i, y_i, z_i)$, derived from a bipolar time-and-point-dependent depolarization signal $S_{BPi}(t, x_i, y_i, z_i)$ acquired from that acquisition point $P_i(x_i, y_i, z_i)$ on or within the heart, that is associated with an absolute maximum power density in the bipolar point-dependent discrete power spectrum $DPS_{BPi}(f, x_i, y_i, z_i)$.

The point-dependent product dominant frequency $DF_{PRODi} (x_i, y_i, z_i)$ of an acquisition point $P_i(x_i, y_i, z_i)$ on or within the heart is the frequency in the point-dependent discrete power spectrum product $DPS_{PRODi}(f, x_i, y_i, z_i)$ obtained by the multiplication of a unipolar point-dependent discrete power spectrum $DPS_{UPi}(f, x_i, y_i, z_i)$ by a corresponding bipolar point-dependent discrete power spectrum $DPS_{BPi}(f, x_i, y_i, z_i)$, each respectively derived from a unipolar time-and-point-dependent depolarization signal $S_{UPi}(t, x_i, y_i, z_i)$ acquired from that acquisition point $P_i(x_i, y_i, z_i)$ on or within the heart and a corresponding bipolar time-and-point-dependent depolarization signal $S_{BPi}(t, x_i, y_i, z_i)$ acquired from the same acquisition point $P_i(x_i, y_i, z_i)$ on or within the heart, that is associated with an absolute maximum power density in the point-dependent discrete power spectrum product $DPS_{PRODi}(f, x_i, y_i, z_i)$.

In any given acquisition of unipolar and bipolar time-and-point-dependent depolarization signals, $S_{UPi}(t, x_i, y_i, z_i)$, $S_{BPi}(t, x_i, y_i, z_i)$, from each point acquisition $P_i(x_i, y_i, z_i)$ of a set of acquisition points $\{P_i(x_i, y_i, z_i)\}$, there will be at least one acquisition point $P_i (x_i, y_i, z_i)$ whose point-dependent product dominant frequency $DF_{PRODi}(x_i, y_i, z_i)$ is associated with a point-dependent maximum product dominant frequency $DF_{MAXPRODi}(x_i, y_i, z_i)$.

7c. Dominant Frequency Band

In the SSFA Identification Method and Algorithm, the term "point-dependent dominant frequency band" ("$\Delta_i DF$") comprises a frequency band of about three times the frequency resolution ("$\Delta f_i$") e.g., about 0.75 Hz, centered about a point-dependent dominant frequency $DF_i$.

7d. Regularity Index

In the SSFA Identification Method and Algorithm, the degree to which the point-dependent dominant frequency $DF_i$ of a time-and point-dependent depolarization signal $S_i (t, x_i, y_i, z_i)$ acquired from an acquisition point $P_i (x_i, y_i, z_i)$ on or within the heart during an episode of fibrillation is an exclusive contributor to the time-and point-dependent depolarization signal $S_i (t, x_i, y_i, z_i)$ is gauged by an associated point-dependent regularity index $RI_i (x_i, y_i, z_i)$ or $RI_i$.

The closer the value of the point-dependent regularity index $RI_i$ is to 1, the fewer the frequencies other than the dominant frequency $DF_i$ that contribute to a time-and-point-dependent depolarization signal $S_i (t, x_i, y_i, z_i)$. Accordingly, if the coordinates of an acquisition point having a particular dominant frequency are assigned to the SSFA, the validity of the assignment may be assessed by interpreting the value of the point-dependent regularity index associated with the dominant frequency. The closer the value of the associated point-dependent regularity index $RI_i$ is to 1, the greater the likelihood that the assignment of coordinates accurately identifies the SSFA.

The value of the point-dependent regularity index $RI_i$ also serves to characterize the behavior of a time-and-point-dependent depolarization signal $S_i (t, x_i, y_i, z_i)$ in the time domain.

The closer the value of the point-dependent regularity index $RI_i$ is to 1, the more regularly periodic the time-and-point-dependent depolarization signal $S_i (t, x_i, y_i, z_i)$. Conversely, the closer the value of the point-dependent regularity index $RI_i$ is to zero, the more irregularly periodic the time-and-point-dependent depolarization signal $S_i (t, x_i, y_i, z_i)$.

Consequently, points near a very stable high-frequency SSFA, or points far from such a SSFA but having very low frequencies, will be associated with point-dependent regularity index $RI_i$ having values close to 1; and, conversely, points near wave front fragmentation or an unstable, meandering high-frequency SSFA, or sites of intermittent conduction delays or blocks, are likely to be associated with point-dependent regularity index $RI_i$ values closer to zero.

The point-dependent regularity index $RI_i$ is defined as the ratio of the power contained in the point-dependent dominant frequency band $\Delta_i DF$ to the total power computed at all frequencies of the point-dependent discrete power spectrum $DPS_i (f, x_i, y_i, z_i)$, the dominant frequency band $\Delta_i DF$ being a frequency band centered about a point-dependent dominant frequency $DF$ having a width of about three times the frequency resolution $\Delta f_i$.

For example, in FIG. 1, regularity indices of 0.33, 0.28 and 0.25 have been computed for the respective dominant frequency peaks found in each of the power spectra of the time-dependent depolarization signals, A, B, C.

By analogy with the forgoing definitions of a unipolar, bipolar and product dominant frequency, a unipolar point-dependent regularity index $RI_{UPi}$ may be computed from a unipolar point-dependent discrete power spectrum $DPS_{UPi}$ (f, $x_i$, $y_i$, $z_i$), a bipolar point-dependent regularity index $RI_{BPi}$ may be computed from a bipolar point-dependent discrete power spectrum $DPS_{BPi}$ (f, $x_i$, $y_i$, $z_i$), and, a product point-dependent regularity index $RI_{BPi}$ may be computed from a point-dependent discrete power spectrum product $DPS_{PRODi}$ (f, $x_i$, $y_i$, $z_i$).

7e. Defining Criterion for Identifying a Point of SSFA: Maximum Dominant Frequency In the SSFA Identification Method and Algorithm, the point of SSFA is assigned the coordinates of that acquisition point $P_i$ ($x_i$, $y_i$, $z_i$) whose point-dependent discrete power spectrum product $DPS_{PRODi}$ (f, $x_i$, $y_i$, $z_i$) has a point-dependent product dominant frequency $DF_{MAXPRODi}$ ($x_i$, $y_i$, $z_i$), that is higher than the point-dependent product dominant frequency $DF_{PRODi}$ ($x_i$, $y_i$, $z_i$) of any other point-dependent discrete power spectrum product $DPS_{PRODi}$ (f, $x_i$, $y_i$, $z_i$) computed for any other acquisition point $P_i$ ($x_i$, $y_i$, $z_i$).

The point-dependent product dominant frequency $DF_{PRODi}$ ($x_i$, $y_i$, $z_i$) satisfying this criterion is called the maximum point-dependent product dominant frequency $DF_{MAXPRODi}$. The spatial coordinates of the maximum point-dependent product dominant frequency $DF_{MAXPRODi}$ identify the point of SSFA.

8. SSFA Identification Method and Algorithm

Figure 5:
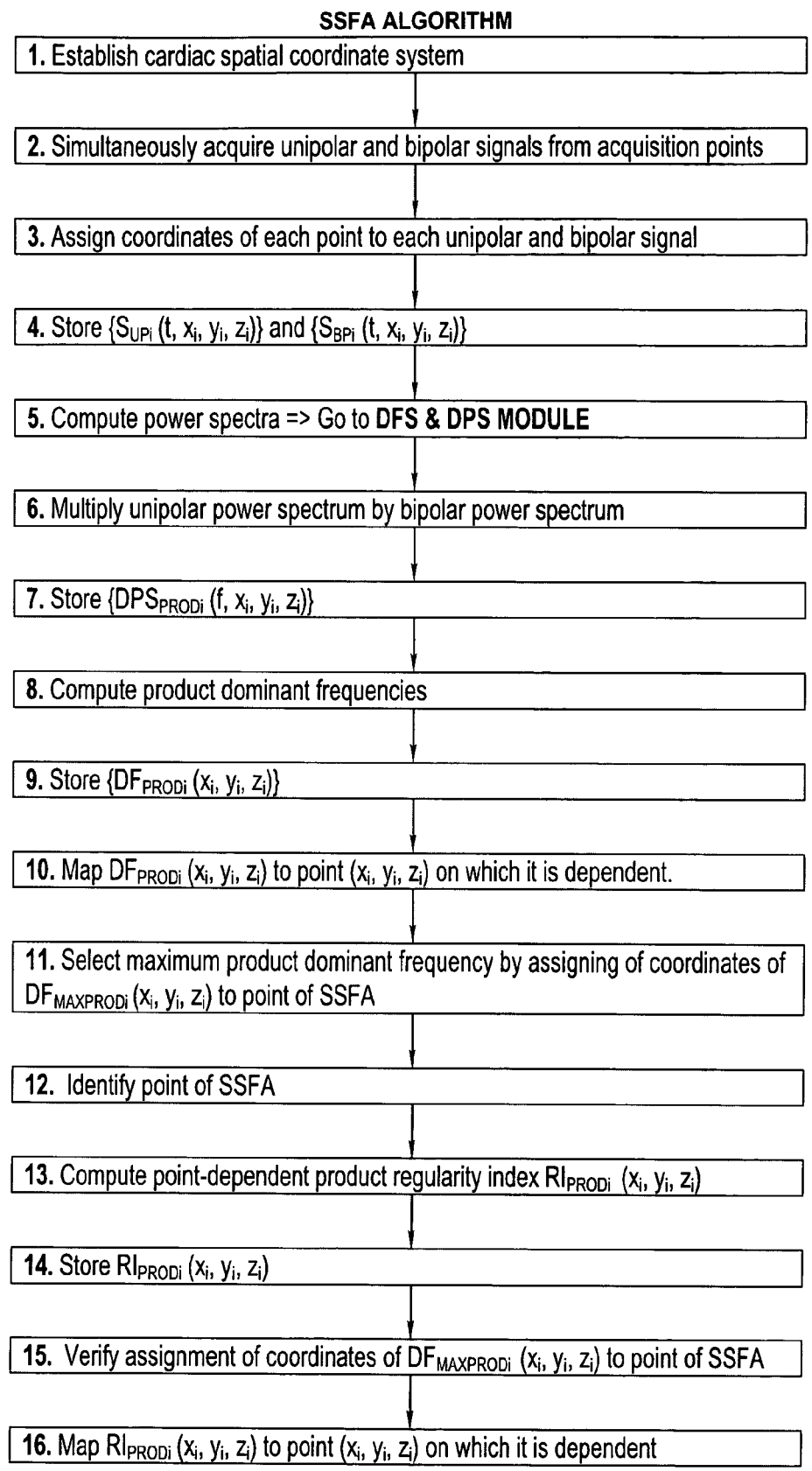
FIG. 5 shows a flowchart that outlines the SSFA Identification Method and Algorithm.

FIG. 5 shows a flowchart that outlines the SSFA Identification Method and Algorithm.

Figure 6:
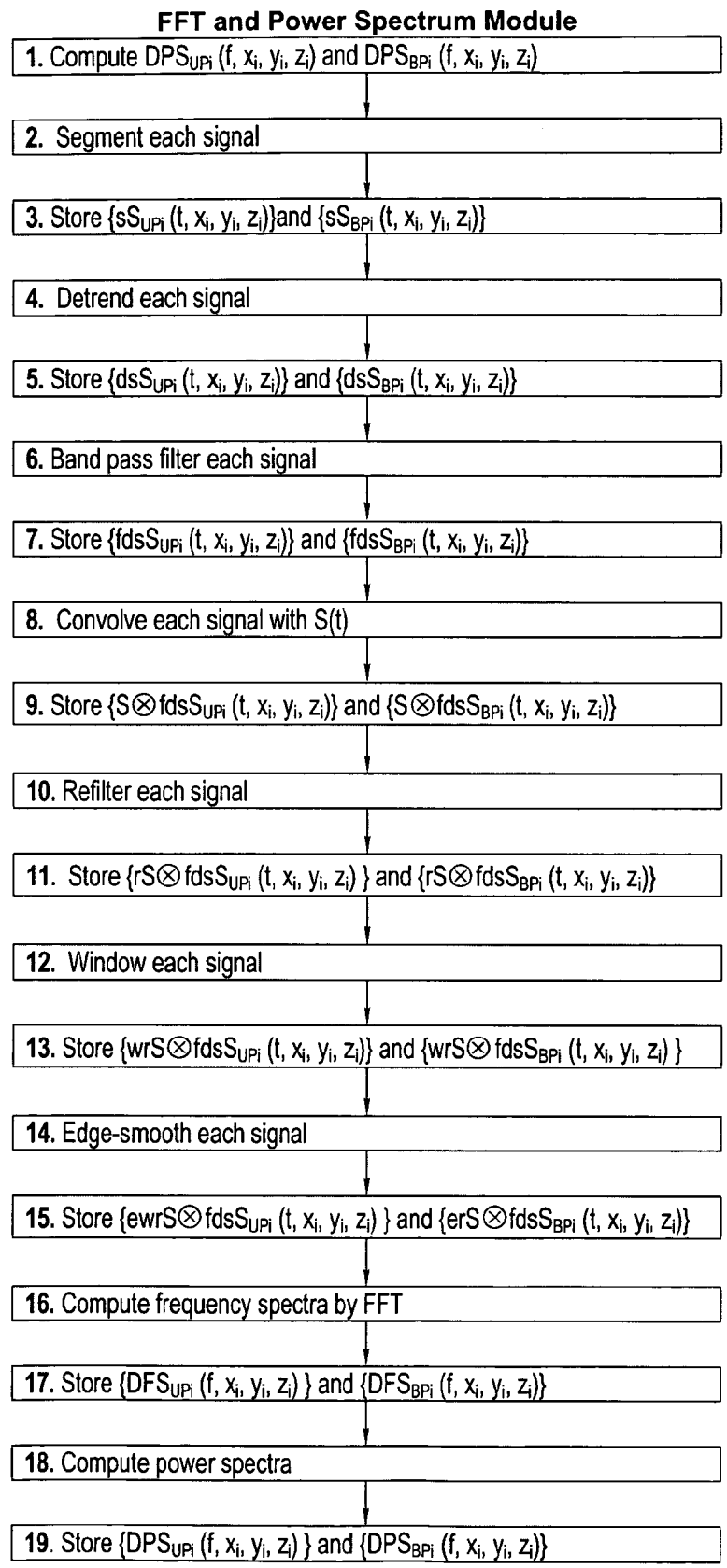
FIG. 6 shows a flowchart that outlines the FFT and Power Spectrum Module of the SSFA Identification Method and Algorithm.

FIG. 6 shows a flowchart that outlines the FFT and Power Spectrum Module of the SSFA Identification Method and Algorithm.

8a. Establish a Cardiac Spatial Coordinate System

Referring initially to Flowchart Step No. 1 in FIG. 5, spatial coordinates ($x_i$, $y_i$, $z_i$) for cardiac points are determined by:

pre-defining a spatial coordinate system (x, y, z) for the identification of cardiac points $cP_i(x_i, y_i, z_i)$ having spatial coordinates ($x_i$, $y_i$, $z_i$) on or within the heart;

storing the cardiac points $cP_i$ ($x_i$, $y_i$, $z_i$) on a computer recordable medium as a set cardiac points $\{cP_i$ ($x_i$, $y_i$, $z_i$)$\}$;

assigning to each acquisition point $P_i(x_i, y_i, z_i)$ the coordinates of the cardiac point with which it is spatially coincident.

The spatial coordinate system and the spatial coordinates may, for example, be maintained in a Cartesian, spherical, cylindrical, conical, or other spatial coordinate system that are transformable inter se. The spatial coordinate system may, for example, be defined by adaptation of the multi-electrode basket method, the CARTO system, or the Ensite non-contact mapping system, all known in the cardiac electrophysiological arts.

8b. Simultaneously Acquire a Unipolar $S_{UPi}(t)$ and Bipolar Signal $S_{BPi}(t)$ from Points During an episode of fibrillation, a unipolar time-dependent depolarization signal $S_{UP}(t)$ and a corresponding bipolar time-dependent depolarization signal $S_{BP}(t)$ are simultaneously acquired by a cardiac acquisition device from each acquisition point $P_i(x_i, y_i, z_i)$ of an acquisition set of points $\{P_i(x_i, y_i, z_i)\}$ of the heart, each acquisition point $P_i$ ($x_i$, $y_i$, $z_i$) having unique spatial coordinates ($x_i$, $y_i$, $z_i$) identified from the pre-stored set of cardiac points $\{cP_i$ ($x_i$, $y_i$, $z_i$)$\}$. (Flowchart Step No. 2 in FIG. 5).

The simultaneously acquired unipolar and bipolar time-dependent depolarization signals $S_{UPi}(t)$, $S_{BPi}(t)$ may be acquired in the aforementioned roving mode, which mode comprises the repetitive sequential use through a plurality of iterations of a roving cardiac signal acquisition device that detects, records and outputs the simultaneously acquired unipolar and bipolar time-dependent depolarization signals $S_{UPi}(t)$, $S_{BPi}(t)$ to a computer recordable medium from each acquisition point $P_i(x_i, y_i, z_i)$. Alternatively, a plurality of paired unipolar and bipolar time-dependent depolarization signals $S_{UPi}(t)$, $S_{BPi}(t)$ may be simultaneously acquired in a concurrent mode, using a concurrent cardiac signal acquisition device that detects, records and outputs a plurality of simultaneously acquired paired unipolar and bipolar time-dependent depolarization signals $S_{UPi}(t)$, $S_{BPi}(t)$ to a computer recordable medium from a plurality of acquisition points $P_i(x_i, y_i, z_i)$.

The simultaneously acquired unipolar and bipolar time-dependent depolarization signals $S_{UPi}(t)$, $S_{BPi}(t)$ may be recorded over an acquisition time of, for example about 5 seconds. The unipolar and bipolar time-dependent depolarization signals $S_{UPi}(t)$, $S_{BPi}(t)$ may be acquired as discretely sampled signals by the roving cardiac signal acquisition device, in which case the acquisition time comprises a sampling time, or they may be acquired as continuous signals that are discretely sampled after their acquisition by means, for example, of a computing device.

8c. Assign Coordinates of Each Point to Each Unipolar and Corresponding Bipolar Signal Forming $S_{UPi}(t, x_i, y_i, z_i)$ and $S_{BPi}(t, x_i, y_i, z_i)$ A set of unipolar time-and-point-dependent depolarization signals $\{S_{UPi}(t, x_i, y_i, z_i)\}$ is formed by assigning to each unipolar time-dependent depolarization signal $S_{UP}(t)$ the spatial coordinates ($x_i$, $y_i$, $z_i$) of the acquisition point $P_i(x_i, y_i, z_i)$ from which it was acquired; and, a set of corresponding bipolar time-and-point-dependent depolarization signals $\{S_{BPi}$ (t, $x_i$, $y_i$, $z_i$)$\}$ is formed by assigning to each corresponding bipolar time-dependent depolarization signal $S_{BP}(t)$ the spatial coordinates ($x_i$, $y_i$, $z_i$) of the acquisition point $P_i(x_i, y_i, z_i)$ from which it was simultaneously acquired (Flowchart Step No. 3 in FIG. 5).

8d. Store $\{S_{UPi}(t, x_i, y_i, z_i)\}$ and $\{S_{BPi}(t, x_i, y_i, z_i)\}$

The set of unipolar time-and-point-dependent depolarization signals $\{S_{UPi}(t, x_i, y_i, z_i)\}$ and the set of corresponding bipolar time-and-point-dependent depolarization signals $\{S_{BPi}$ (t, $x_i$, $y_i$, $z_i$)$\}$ are respectively stored on a computer recordable medium (Flowchart Step No. 4 in FIG. 5).

8e. Compute Power Spectra $DPS_{UPi}$ (f, $x_i$, $y_i$, $z_i$) and $DPS_{BPi}$ (f, $x_i$, $y_i$, $z_i$)

A set of unipolar point-dependent discrete power spectra $\{DPS_{UPi}(f, x_i, y_i, z_i)\}$ is formed by computing a unipolar point-dependent discrete power spectrum $DPS_{UPi}(f, x_i, y_i, z_i)$ for each unipolar time-and-point-dependent depolarization signal $\{S_{UPi}$ (t, $x_i$, $y_i$, $z_i$)$\}$; and, a set of bipolar point-dependent discrete power spectra $\{DPS_{BPi}(f, x_i, y_i, z_i)\}$ is formed by computing a bipolar point-dependent discrete power spectrum $DPS_{BPi}(f, x_i, y_i, z_i)$ for each corresponding bipolar time-and-point-dependent depolarization signal $\{S_{BPi}(t, x_i, y_i, z_i)\}$ (Flowchart Step No. 5 in FIG. 5).

Referring now to Flowchart Step No. 1 in FIG. 6, each unipolar point-dependent discrete power spectrum $DPS_{UPi}$ (f, $x_i$, $y_i$, $z_i$) of the set of the set of unipolar point-dependent discrete power spectra {$DPS_{UPi}$(f, $x_i$, $y_i$, $z_i$)} and each bipolar point-dependent discrete power spectrum $DPS_{BPi}$(f, $x_i$, $y_i$, $z_i$) of the set of bipolar point-dependent discrete power spectra {$DPS_{BPi}$(f, $x_i$, $y_i$, $z_i$)} is computed as follows:

8e(i). Segment Each Signal

A predefined segment of each unipolar time-and-point-dependent depolarization signal $S_{UPi}$ (t, $x_i$, $y_i$, $z_i$), such as, for example, 5 ms, is selected, thereby forming a set of segmented unipolar time and-point-dependent depolarization signals {$sS_{UPi}$(t, $x_i$, $y_i$, $z_i$)}; and, a predefined segment of each of the corresponding bipolar time-and-point-dependent depolarization signal $S_{BPi}$ (t, $x_i$, $y_i$, $z_i$), such as, for example, 5 ms, is selected thereby forming a set of corresponding segmented bipolar time-and-point-dependent depolarization signals {$sS_{BPi}$ (t, $x_i$, $y_i$, $z_i$)} (Flowchart Step No. 2 in FIG. 6).

8e(ii). Store {$sS_{UPi}$(t, $x_i$, $y_i$, $z_i$)} and {$sS_{BPi}$(t, $x_i$, $y_i$, $z_i$)}

The set of segmented unipolar time-and-point-dependent depolarization signals {$sS_{UPi}$ (t, $x_i$, $y_i$, $z_i$)} is stored on a computer recordable medium and the set of corresponding segmented bipolar time and-point-dependent depolarization signals {$sS_{BPi}$ (t, $x_i$, $y_i$, $z_i$)} is also stored on a computer recordable medium (Flowchart Step No. 3 in FIG. 6).

8e(iii). Detrend Each Signal

Each segmented unipolar time-and-point-dependent depolarization signal $sS_{UPi}$ (t, $x_i$, $y_i$, $z_i$) is detrended, that is, a linear best fit vector of $sS_{UPi}$(t, $x_i$, $y_i$, $z_i$) is computed and its magnitude is subtracted from the values of $sS_{UPi}$(t, $x_i$, $y_i$, $z_i$) at each point in time, thereby forming a set of detrended and segmented unipolar time-and-point-dependent depolarization signals {$dsS_{UPi}$(t, $x_i$, $y_i$, $z_i$)}; and, each corresponding segmented bipolar time-and-point-dependent depolarization signal $sS_{BPi}$(t, $x_i$, $y_i$, $z_i$) is also detrended, thereby forming a set of corresponding detrended and segmented bipolar time and-point-dependent depolarization signals {$dsS_{BPi}$ (t, $x_i$, $y_i$, $z_i$)} (Flowchart Step No. 4 in FIG. 6).

8e(iv). Store {$dsS_{UPi}$(t, $x_i$, $y_i$, $z_i$)} and {$dsS_{BPi}$ (t, $x_i$, $y_i$, $z_i$)}

The set of detrended and segmented unipolar time-and-point-dependent depolarization signals {$dsS_{UPi}$ (t, $x_i$, $y_i$, $z_i$)} is stored on a computer recordable medium; and the set of corresponding detrended and segmented bipolar time and-point-dependent depolarization signals {$dsS_{BPi}$ (t, $x_i$, $y_i$, $z_i$)} is also stored on a computer recordable medium (Flowchart Step No. 5 in FIG. 6).

8e(v). Band Pass Filtering Each Signal

Each detrended and segmented unipolar time-and-point-dependent depolarization signal $dsS_{UPi}$ (t, $x_i$, $y_i$, $z_i$) band pass-filtered between a first frequency limit $F_{lim1}$ and a second frequency limit $F_{lim2}$. The first frequency limit may be about 1 Hz and the second frequency limit may be about 30 Hz. This band pass-filtering forms a set of filtered, detrended and segmented unipolar time and-point-dependent depolarization signals {$fdsS_{UPi}$ (t, $x_i$, $y_i$, $z_i$)}. Each corresponding detrended and segmented bipolar time-and-point-dependent depolarization signal $dsS_{BPi}$ (t, $x_i$, $y_i$, $z_i$) is also band pass-filtered between the first frequency limit $F_{lim1}$ and the second frequency limit $F_{lim2}$, thereby forming a set of corresponding filtered, detrended and segmented bipolar time-and-point-dependent depolarization signals {$fdsS_{BPi}$ (t, $x_i$, $y_i$, $z_i$)} (Flowchart Step No. 6 in FIG. 6).

8e(vi). Store {$fdsS_{UPi}$(t, $x_i$, $y_i$, $z_i$)} and {$fdsS_{BPi}$(t, $x_i$, $y_i$, $z_i$)}

The set of filtered, detrended and segmented unipolar time-and-point-dependent depolarization signals {$fdsS_{UPi}$ (t, $x_i$, $y_i$, $z_i$)} is stored on a computer recordable medium; and the set of corresponding filtered, detrended and segmented bipolar time and-point-dependent depolarization signals {$fdsS_{BPi}$ (t, $x_i$, $y_i$, $z_i$)} is also stored on a computer recordable medium (Flowchart Step No. 7 in FIG. 6).

8e(vii). Convolve Each Signal with $\mathbf{s}$(t)

Each filtered, segmented and detrended unipolar time-and-point-dependent depolarization signal $fdsS_{UPi}$ (t, $x_i$, $y_i$, $z_i$) is convolved with a shaping signal $\mathbf{s}$(t), thereby forming a set of shaped, filtered, detrended and segmented unipolar time-and-point-dependent depolarization signals {$\mathbf{s}fdsS_{UPi}$ (t, $x_i$, $y_i$, $z_i$)}; and, each corresponding filtered, detrended and segmented bipolar time-and-point-dependent depolarization signal $fdsS_{BPi}$(t, $x_i$, $y_i$, $z_i$) with also convolved with the shaping signal $\mathbf{s}$(t), thereby forming a set of corresponding shaped, filtered, detrended and segmented bipolar time-and-point-dependent depolarization signals {$\mathbf{s}fdsS_{BPi}$ (t, $x_i$, $y_i$, $z_i$)} (Flowchart Step No. 8 in FIG. 6).

The shaping signal may, for example comprise a time-dependent periodic triangle having a base of 100 ms and unit amplitude. The effect of each convolution is to clarify each filtered, segmented and detrended unipolar time-and-point-dependent depolarization signal $fdsS_{UPi}$ (t, $x_i$, $y_i$, $z_i$) and to clarify each filtered, segmented and detrended bipolar time-and-point-dependent depolarization signal $fdsS_{BPi}$ (t, $x_i$, $y_i$, $z_i$).

8e(viii). Store {$\mathbf{s}fdsS_{UPi}$ (t, $x_i$, $y_i$, $z_i$)} and {$\mathbf{s}fdsS_{BPi}$ (t, $x_i$, $y_i$, $z_i$)}

The set of shaped, filtered, detrended and segmented unipolar time-and-point-dependent depolarization signals {$\mathbf{s}fdsS_{UPi}$ (t, $x_i$, $y_i$, $z_i$)} is stored on a computer recordable medium and the set of corresponding shaped, filtered, detrended and segmented bipolar time and-point-dependent depolarization signals {$\mathbf{s}fdsS_{BPi}$ (t, $x_i$, $y_i$, $z_i$)} is also stored on a computer recordable medium (Flowchart Step No. 9 in FIG. 6).

8e(ix). Refilter Each Signal

Each shaped, filtered, segmented and detrended unipolar time-and-point-dependent depolarization signal $\mathbf{s}fdsS_{UPi}$ (t, $x_i$, $y_i$, $z_i$) is again band pass-filtered between a third frequency limit $F_{lim3}$ and a fourth frequency limit $F_{lim4}$. The third frequency limit may be about 1 Hz and the fourth frequency may be about 30 Hz. This band pass-filtering forms a set of refiltered, shaped, filtered, detrended and segmented unipolar time-and-point-dependent depolarization signals {$r\mathbf{s}fdsS_{UPi}$ (t, $x_i$, $y_i$, $z_i$)}. Each shaped, filtered, detrended and segmented bipolar time-and-point-dependent depolarization signal $\mathbf{s}fdsS_{BPi}$ (t, $x_i$, $y_i$, $z_i$) is also band pass filtered between the third frequency limit $F_{lim3}$ and the fourth frequency limit $F_{lim4}$, thereby forming a set of corresponding refiltered, shaped, filtered, detrended and segmented bipolar time-and-point-dependent depolarization signals {$r\mathbf{s}fdsS_{BPi}$ (t, $x_i$, $y_i$, $z_i$)}. (Flowchart Step No. 10 in FIG. 6).

8e(x). Store {$r\mathbf{s}fdsS_{UPi}$ (t, $x_i$, $y_i$, $z_i$)} and {$r\mathbf{s}fdsS_{BPi}$ (t, $x_i$, $y_i$, $z_i$)}

The set of refiltered, shaped, filtered, detrended and segmented unipolar time-and-point-dependent depolarization signals {$r\mathbf{s}fdsS_{UPi}$ (t, $x_i$, $y_i$, $z_i$)} is stored on a computer recordable medium and the set of corresponding refiltered, shaped, filtered, detrended and segmented bipolar time and-point-dependent depolarization signals {$r\mathbf{s}fdsS_{BPi}$ (t, $x_i$, $y_i$, $z_i$)} is also stored on a computer recordable medium (Flowchart Step No. 11 in FIG. 6).

8e(xi). Window Each Signal

Each refiltered, shaped, filtered, detrended and segmented unipolar time-and-point-dependent depolarization signal $rsfdsS_{UPi}$ (t, $x_i$, $y_i$, $z_i$) is windowed. A window may, for example, be selected having a power-of-2-length in the center of the refiltered, shaped, filtered, detrended and segmented unipolar time-and-point-dependent depolarization signal $rsfdsS_{UPi}$ (t, $x_i$, $y_i$, $z_i$), and may correspond to a default of 4096 discretely sampled points. Windowing of each refiltered, shaped, filtered, detrended and segmented unipolar time-and-point-dependent depolarization signal $rsfdsS_{UPi}$(t, $x_i$, $y_i$, $z_i$) forms a set of windowed, refiltered, shaped, filtered, detrended and segmented unipolar time-and-point-dependent depolarization signals $\{wrsfdsS_{UPi}$ (t, $x_i$, $y_i$, $z_i$)$\}$. Each corresponding refiltered, shaped, filtered, detrended and segmented bipolar time-and-point-dependent depolarization signal $rsfdsS_{BPi}$(t, $x_i$, $y_i$, $z_i$), is also windowed, thereby forming a set of corresponding windowed, refiltered, shaped, filtered, detrended and segmented bipolar time-and-point-dependent depolarization signals $\{wrsfdsS_{BPi}$ (t, $x_i$, $y_i$, $z_i$)$\}$. (Flowchart Step No. 12 in FIG. 6).

8e(xii). Store $\{wrsfdsS_{UPi}(t, x_i, y_i, z_i)\}$ and $\{rsfdsS_{BPi}$ (t, $x_i$, $y_i$, $z_i$)$\}$ The set of windowed, refiltered, shaped, filtered, detrended and segmented unipolar time-and-point-dependent depolarization signals $\{wrsfdsS_{UPi}$ (t, $x_i$, $y_i$, $z_i$)$\}$ is stored on a computer recordable medium and the set of corresponding windowed, refiltered, shaped, filtered, detrended and segmented bipolar time and-point-dependent depolarization signals $\{wrsfdsS_{BPi}$ (t, $x_i$, $y_i$, $z_i$)$\}$ is also stored on a computer recordable medium (Flowchart Step No. 13 in FIG. 6).

8e(xiii). Edge-Smooth Each Signal

Each windowed, refiltered, shaped, filtered, segmented and detrended unipolar time-and-point-dependent depolarization signal $wrsfdsS_{UPi}$ (t, $x_i$, $y_i$, $z_i$) is edge-smoothed, so that its beginning and end gradually converge to a value of zero. This can be achieved by multiplying it with a preselectable window, such as, for example, a Hanning window. Edge-smoothing each windowed, refiltered, shaped, filtered, segmented and detrended unipolar time-and-point-dependent depolarization signal $wrsfdsS_{UPi}$ (t, $x_i$, $y_i$, $z_i$) forms a set of edge-smoothed, windowed, refiltered, shaped, filtered, detrended and segmented unipolar time-and-point-dependent depolarization signals $\{ewrsfdsS_{UPi}(t, x_i, y_i, z_i)\}$. Each corresponding windowed, refiltered, shaped, filtered, detrended and segmented bipolar time-and-point-dependent depolarization signal $wrsfdsS_{BPi}$ (t, $x_i$, $y_i$, $z_i$) is also edge-smoothed, thereby forming a set of corresponding edge-smoothed, windowed, refiltered, shaped, filtered, detrended and segmented bipolar time-and-point-dependent depolarization signals $\{ewrsfdsS_{BPi}$ (t, $x_i$, $y_i$, $z_i$)$\}$. (Flowchart Step No. 14 in FIG. 6).

8e(xiv). Store $\{ewrsfdsS_{UPi}(t, x_i, y_i, z_i)\}$ and $\{ersfdsS_{BPi}$ (t, $x_i$, $y_i$, $z_i$)$\}$ The set of edge-smoothed, windowed, refiltered, shaped, filtered, detrended and segmented unipolar time-and-point-dependent depolarization signals $\{ewrsfdsS_{UPi}(t, x_i, y_i, z_i)\}$ is stored on a computer recordable medium and the set of corresponding edge-smoothed, windowed, refiltered, shaped, filtered, detrended and segmented bipolar time and-point-dependent depolarization signals $\{ersfdsS_{BPi}(t, x_i, y_i, z_i)\}$ is also stored on a computer recordable medium (Flowchart Step No. 15 in FIG. 6).

8e(xv). Compute Frequency Spectra Using an FFT

A unipolar point-dependent discrete frequency spectrum is computed for each edge-smoothed, windowed, refiltered, shaped, filtered, segmented and detrended unipolar time-and-point-dependent depolarization signal $ewrsfdsS_{UPi}$ (t, $x_i$, $y_i$, $z_i$), by means of a Fast Fourier Transform, thereby forming a set of unipolar point-dependent discrete frequency spectra $\{DFS_{UPi}(f, x_i, y_i, z_i)\}$; and, a bipolar point-dependent discrete frequency spectrum is computed for each edge-smoothed, windowed, refiltered, shaped, filtered, segmented and detrended bipolar time-and-point-dependent depolarization signal $ewrsfdsS_{BPi}$ (t, $x_i$, $y_i$, $z_i$), by means of a Fast Fourier Transform, thereby forming the set of bipolar point-dependent discrete frequency spectra $\{DFS_{BPi}(f, x_i, y_i, z_i)\}$ (Flowchart Step No. 16 in FIG. 6).

8e(xvi). Store $\{DFS_{UPi}$ (f, $x_i$, $y_i$, $z_i$)$\}$ and $\{DFS_{BPi}$ (f, $x_i$, $y_i$, $z_i$)$\}$ The set of unipolar point-dependent discrete frequency spectra $\{DFS_{UPi}$ (f, $x_i$, $y_i$, $z_i$)$\}$ is stored on a computer recordable medium and the set of bipolar point-dependent discrete frequency spectra $\{DFS_{BPi}$ (f, $x_i$, $y_i$, $z_i$)$\}$ is also stored on a computer recordable medium (Flowchart Step No. 17 in FIG. 6).

8e(xvii). Compute Power Spectra

A unipolar point-dependent discrete power spectrum is computed for each edge-smoothed, windowed, refiltered, shaped, filtered, segmented and detrended unipolar time-and-point-dependent depolarization signal $ewrsfdsS_{UPi}$ (t, $x_i$, $y_i$, $z_i$), thereby forming a set of unipolar point-dependent discrete power spectra $\{DPS_{UPi}(f, x_i, y_i, z_i)\}$; and, a bipolar point-dependent discrete power spectrum is computed for each edge-smoothed, windowed, refiltered, shaped, filtered, segmented and detrended bipolar time-and-point-dependent depolarization signal $ewrsfdsS_{BPi}$ (t, $x_i$, $y_i$, $z_i$), thereby forming a set of bipolar point-dependent discrete power spectra $\{DPS_{BPi}(f, x_i, y_i, z_i)\}$ (Flowchart Step No. 18 in FIG. 6).

8e(xviii). Store $\{DPS_{UPi}$ (f, $x_i$, $y_i$, $z_i$)$\}$ and $\{DPS_{BPi}$ (f, $x_i$, $y_i$, $z_i$)$\}$ The set of unipolar point-dependent discrete power spectra $\{DPS_{UPi}$ (f, $x_i$, $y_i$, $z_i$)$\}$ is stored on a computer recordable medium and the set of bipolar point-dependent discrete power spectra $\{DPS_{BPi}$ (f, $x_i$, $y_i$, $z_i$)$\}$ is also stored on a computer recordable medium (Flowchart Step No. 19 in FIG. 6).

8f. Multiply Unipolar Power Spectrum by Bipolar Power Spectrum

Returning now to Flowchart Step 6 of FIG. 5, a set of point-dependent discrete power spectrum products $\{DPS_{PRODi}$ (f, $x_i$, $y_i$, $z_i$)$\}$ is formed by multiplying each unipolar point-dependent discrete power spectrum $DPS_{UPi}(f, x_i, y_i, z_i)$ of the set of unipolar point-dependent discrete power spectra $\{DPS_{UPi}$ (f, $x_i$, $y_i$, $z_i$)$\}$ by each the corresponding bipolar point-dependent discrete power spectrum $DPS_{BPi}(f, x_i, y_i, z_i)$ of the set of corresponding bipolar point-dependent discrete power spectra $\{DPS_{BPi}$ (f, $x_i$, $y_i$, $z_i$)$\}$.

8g. Store $\{DPS_{PRODi}$ (f, $x_i$, $y_i$, $z_i$)$\}$

The set of point-dependent discrete power spectrum products $\{DPS_{PRODi}$ (f, $x_i$, $y_i$, $z_i$)$\}$ is stored on a computer recordable medium (Flowchart Step 7 of FIG. 5).

8h. Compute Product Dominant Frequencies

A point-dependent product dominant frequency $DF_{PRODi}$ ($x_i$, $y_i$, $z_i$) is computed for each point-dependent discrete product power spectrum $DPS_{PRODi}(f, x_i, y_i, z_i)$ of the set of point-dependent discrete power spectrum products $\{DPS_{PRODi}(f, x_i, y_i, z_i)\}$, thereby forming a set of point-dependent product dominant frequencies $\{DF_{PRODi}(x_i, y_i, z_i)\}$ (Flowchart Step 8 of FIG. 5).

8i. Store $\{DF_{PRODi}(x_i, y_i, z_i)\}$

The set of point-dependent product dominant frequencies $\{DF_{PRODi}(x_i, y_i, z_i)\}$ is stored on a computer recordable medium (Flowchart Step 9 of FIG. 5).

8j. Map $DF_{PRODi}(x_i, y_i, z_i)$ to the point $(x_i, y_i, z_i)$ on which it is Dependent.

Each point-dependent product dominant frequency $DF_{PRODi}(x_i, y_i, z_i)$ of the set of point-dependent product dominant frequencies $\{DF_{PRODi}(x_i, y_i, z_i)\}$ is mapped to the point $(x_i, y_i, z_i)$ with which it is associated (Flowchart Step 10 of FIG. 5).

8k. Select the Maximum Dominant Frequency

A maximum point-dependent product dominant frequency $DF_{MAXPRODi}(x_i, y_i, z_i)$ is selected from the set of point-dependent product dominant frequencies $\{DF_{PRODi}(x_i, y_i, z_i)\}$ (Flowchart Step 11 of FIG. 5).

8l. Identify the Point of SSFA

The coordinates of the maximum point-dependent product dominant frequency $DF_{MAXPRODi}(x_i, y_i, z_i)$ are assigned to the point of SSFA (Flowchart Step 12 of FIG. 5).

8m. Compute Point-Dependent Product Regularity Index $RI_{PRODi}(x_i, y_i, z_i)$ A point-dependent product regularity index $RI_{PRODi}(x_i, y_i, z_i)$ is computed for each point-dependent discrete product power spectrum $DPS_{PRODi}(f, x_i, y_i, z_i)$ of the set of point-dependent discrete power spectrum products $\{DPS_{PRODi}(f, x_i, y_i, z_i)\}$, thereby forming a set of point-dependent product regularity indices $\{RI_{PRODi}(x_i, y_i, z_i)\}$ (Flowchart Step 13 of FIG. 5).

8n. Store $\{RI_{PRODi}(x_i, y_i, z_i)\}$

The set of point-dependent product regularity indices $\{RI_{PRODi}(x_i, y_i, z_i)\}$ is stored on a computer recordable medium (Flowchart Step 14 of FIG. 5).

8o. Verify the Assignment of the Coordinates of $DF_{MAXPRODi}(x_i, y_i, z_i)$ to the Point of SSFA The assignment of the coordinates of the maximum point-dependent product dominant frequency $DF_{MAXPRODi}(x_i, y_i, z_i)$ to the SSFA is verified by interpreting the value of its corresponding point-dependent product regularity index $RI_{PRODi}(x_i, y_i, z_i)$ (Flowchart Step 15 of FIG. 5)

8p. Map $RI_{PRODi}(x_i, y_i, z_i)$ to the Point $(x_i, y_i, z_i)$ on which it is Dependent.

Each point-dependent product regularity index $RI_{PRODi}(x_i, y_i, z_i)$ of the set of point-dependent product regularity indices $\{RI_{PRODi}(x_i, y_i, z_i)\}$ is mapped to the point $(x_i, y_i, z_i)$ with which it is associated (Flowchart Step 16 of FIG. 5).

9. Computer System

Figure 7:
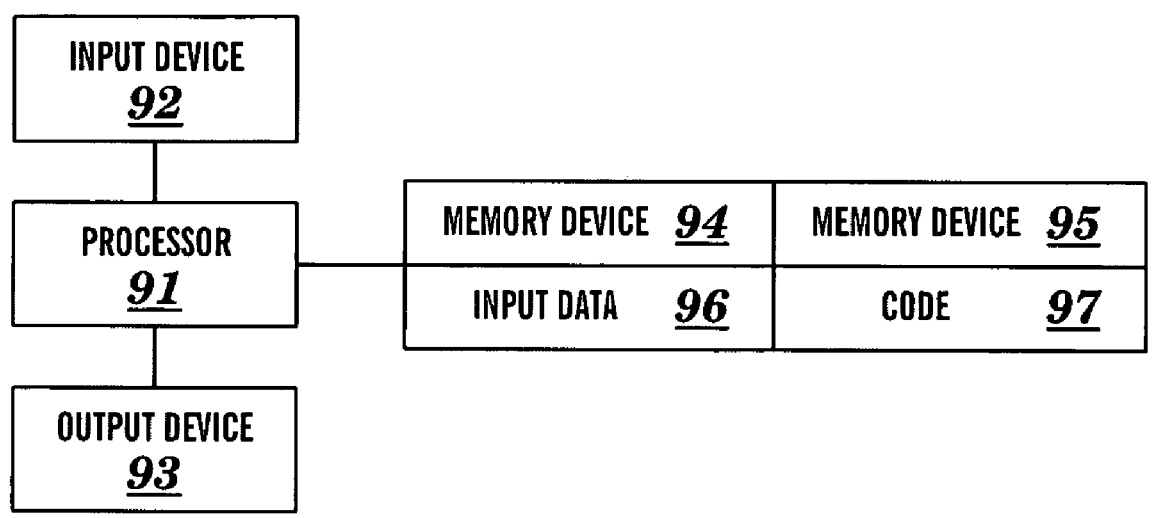
FIG. 7 schematically illustrates a computer system for implementing the SSFA Identification Algorithm, in accordance with embodiments of the present invention.

FIG. 7 illustrates a computer system 90 for implementing the SSFA Identification Algorithm, in accordance with embodiments of the present invention. A computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, an optical storage such as a compact disc (CD), etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes the SSFA Identification Algorithm. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 7) may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise the computer usable medium (or the program storage device).

While FIG. 7 shows the computer system 90 as a particular configuration of hardware and software, any configuration of hardware and software, as would be known to a person of ordinary skill in the art, may be utilized for the purposes stated supra in conjunction with the particular computer system 90 of FIG. 3. For example, the memory devices 94 and 95 may be portions of a single memory device rather than separate memory devices.

We claim:

1. A method for identifying the spatial coordinates of at least one sustaining source of fibrillatory activity ("SSFA") in a heart, said method comprising the steps of:

a. simultaneously acquiring a unipolar time-dependent depolarization signal $S_{UP}(t)$ and a corresponding bipolar time-dependent depolarization signal $S_{BP}(t)$ from each acquisition point $P_i(x_i, y_i, z_i)$ of an acquisition set of points $\{P_i(x_i, y_i, z_i)\}$ on or within said heart, each said acquisition point $P_i(x_i, y_i, z_i)$ having unique spatial coordinates $(x_i, y_i, z_i)$ identified from a set of cardiac points $\{cP_i(x_i, y_i, z_i)\}$;

b. forming a set of unipolar time-and-point-dependent depolarization signals $\{S_{UPi}(t, x_i, y_i, z_i)\}$ by assigning to each said unipolar time-dependent depolarization signal $S_{UP}(t)$ the spatial coordinates $(x_i, y_i, z_i)$ of the acquisition point $P_i(x_i, y_i, z_i)$ from which it was acquired; and, forming a set of corresponding bipolar time-and-point-dependent depolarization signals $\{S_{BPi}(t, x_i, y_i, z_i)\}$ by assigning to each said corresponding bipolar time-dependent depolarization signal $S_{BP}(t)$ the spatial coordinates $(x_i, y_i, z_i)$ of the acquisition point $P_i(x_i, y_i, z_i)$ from which it was simultaneously acquired;

c. forming a set of unipolar point-dependent discrete power spectra $\{DPS_{UPi}(f, x_i, y_i, z_i)\}$ by computing a unipolar point-dependent discrete power spectrum $DPS_{UPi}(f, x_i, y_i, z_i)$ for each said unipolar time-and-point-dependent depolarization signal $S_{UPi}(t, x_i, y_i, z_i)$; and, forming a set of corresponding bipolar point-dependent discrete power spectra $\{DPS_{BPi}(f, x_i, y_i, z_i)\}$ by computing a corresponding bipolar point-dependent discrete power spectrum $DPS_{BPi}(f, x_i, y_i, z_i)$ for each said corresponding bipolar time-and-point-dependent depolarization signal $S_{BPi}(t, x_i, y_i, z_i)$;

d. forming a set of point-dependent discrete power spectrum products $\{DPS_{PRODi}(f, x_i, y_i, z_i)\}$ by multiplying each said unipolar point-dependent discrete power spectrum $DPS_{UPi}(f, x_i, y_i, z_i)$ of said set of unipolar point-dependent discrete power spectra $\{DPS_{UPi}(f, x_i, $y_i$, $z_i$)} by each said corresponding bipolar point-dependent discrete power spectrum $DPS_{BPi}(f, x_i, y_i, z_i)$ of said set of corresponding bipolar point-dependent discrete power spectra {$DPS_{BPi}(f, x_i, y_i, z_i)$};

e. computing a point-dependent product dominant frequency $DF_{PRODi}(x_i, y_i, z_i)$ for each point-dependent discrete power spectrum product $DPS_{PRODi}(f, x_i, y_i, z_i)$, thereby forming a set of point-dependent product dominant frequencies {$DF_{PRODi}(x_i, y_i, z_i)$};

f. selecting a maximum point-dependent product dominant frequency $DF_{MAXPRODi}(x_i, y_i, z_i)$ from said set of point-dependent product dominant frequencies {$DF_{PRODi}(x_i, y_i, z_i)$};

g. assigning the coordinates of said maximum point-dependent product dominant frequency $DF_{MAXPRODi}(x_i, y_i, z_i)$ to said at least one SSFA.

2. The method of claim 1, wherein said unique spatial coordinates ($x_i$, $y_i$, $z_i$) of each said acquisition point $P_i(x_i, y_i, z_i)$, are determined by:

a. defining a spatial coordinate system (x, y, z) for the identification of cardiac points $cP_i(x_i, y_i, z_i)$ having spatial coordinates ($x_i$, $y_i$, $z_i$) on or within said heart;

b. forming said cardiac points $cP_i(x_i, y_i, z_i)$ into a set cardiac points {$cP_i(x_i, y_i, z_i)$};

c. assigning to each acquisition point $P_i(x_i, y_i, z_i)$ the coordinates of the cardiac point with which it is spatially coincident.

3. The method of claim 1, wherein said step of computing a unipolar point-dependent discrete power spectrum $DPS_{UPi}(f, x_i, y_i, z_i)$ for each said unipolar time-and-point-dependent depolarization signal $S_{UPi}(t, x_i, y_i, z_i)$ and computing a corresponding bipolar point-dependent discrete power spectrum $DPS_{BPi}(f, x_i, y_i, z_i)$ for each said corresponding bipolar time-and-point-dependent depolarization signal $S_{BPi}(t, x_i, y_i, z_i)$, further comprises the steps of:

a. selecting a predefined segment of each said unipolar time-and-point-dependent depolarization signal $S_{UPi}(t, x_i, y_i, z_i)$, thereby forming a set of segmented unipolar time and-point-dependent depolarization signals {$sS_{UPi}(t, x_i, y_i, z_i)$}; and, selecting a predefined segment of each of said corresponding bipolar time-and-point-dependent depolarization signal $S_{BPi}(t, x_i, y_i, z_i)$, thereby forming a set of corresponding segmented bipolar time-and-point-dependent depolarization signals {$sS_{BPi}(t, x_i, y_i, z_i)$};

b. detrending each said segmented unipolar time-and-point-dependent depolarization signal $sS_{UPi}(t, x_i, y_i, z_i)$, thereby forming a set of detrended and segmented unipolar time-and-point-dependent depolarization signals {$dsS_{UPi}(t, x_i, y_i, z_i)$}; and, detrending each said corresponding segmented bipolar time-and-point-dependent depolarization signal $sS_{BPi}(t, x_i, y_i, z_i)$, thereby forming a set of corresponding detrended and segmented bipolar time and-point-dependent depolarization signals {$dsS_{BPi}(t, x_i, y_i, z_i)$};

c. band pass filtering each said detrended and segmented unipolar time-and-point-dependent depolarization signal $dsS_{UPi}(t, x_i, y_i, z_i)$ between a first frequency limit $F_{lim1}$ and a second frequency limit $F_{lim2}$, thereby forming a set of filtered, detrended and segmented unipolar time and-point-dependent depolarization signals {$fdsS_{UPi}(t, x_i, y_i, z_i)$}; and, band pass filtering each said corresponding detrended and segmented bipolar time-and-point-dependent depolarization signal $dsS_{BPi}(t, x_i, y_i, z_i)$ between said first frequency limit $F_{lim1}$ and said second frequency limit $F_{lim2}$, thereby forming a set of corresponding filtered, detrended and segmented bipolar time-and-point-dependent depolarization signals {$fdsS_{BPi}(t, x_i, y_i, z_i)$};

d. convolving each said filtered, segmented and detrended unipolar time-and-point-dependent depolarization signal $fdsS_{UPi}(t, x_i, y_i, z_i)$ with a shaping signal $s(t)$, thereby forming a set of shaped, filtered, detrended and segmented unipolar time-and-point-dependent depolarization signals {$s\,fdsS_{UPi}(t, x_i, y_i, z_i)$}; and, convolving each said corresponding filtered, detrended and segmented bipolar time-and-point-dependent depolarization signal $fdsS_{BPi}(t, x_i, y_i, z_i)$ with said shaping signal $s(t)$, thereby forming a set of corresponding shaped, filtered, detrended and segmented bipolar time-and-point-dependent depolarization signals {$s\,fdsS_{BPi}(t, x_i, y_j, z_i)$};

e. band pass filtering each said shaped, filtered, segmented and detrended unipolar time-and-point-dependent depolarization signal $s\,fdsS_{UPi}(t, x_i, y_i, z_i)$ between a third frequency limit $F_{lim3}$ and a fourth frequency limit $F_{lim4}$, thereby forming a set of refiltered, shaped, filtered, detrended and segmented unipolar time-and-point-dependent depolarization signals {$rs\,fdsS_{UPi}(t, x_i, y_i, z_i)$}; and, band pass filtering each said corresponding shaped, filtered, detrended and segmented bipolar time-and-point-dependent depolarization signal $s\,fdsS_{BPi}(t, x_i, y_i, z_i)$ between said third frequency limit $F_{lim3}$ and said fourth frequency limit $F_{lim4}$, thereby forming a set of corresponding refiltered, shaped, filtered, detrended and segmented bipolar time-and-point-dependent depolarization signals {$rs\,fdsS_{BPi}(t, x_i, y_i, z_i)$};

f. windowing each said refiltered, shaped, filtered, detrended and segmented unipolar time-and-point-dependent depolarization signal $rs\,fdsS_{UPi}(t, x_i, y_i, z_i)$, thereby forming a set of windowed, refiltered, shaped, filtered, detrended and segmented unipolar time-and-point-dependent depolarization signals {$wrs\,fdsS_{UPi}(t, x_i, y_i, z_i)$} and, windowing each said corresponding refiltered, shaped, filtered, detrended and segmented bipolar time-and-point-dependent depolarization signal $rs\,fdsS_{BPi}(t, x_i, y_i, z_i)$, thereby forming a set of corresponding windowed, refiltered, shaped, filtered, detrended and segmented bipolar time-and-point-dependent depolarization signals {$wrs\,fdsS_{BPi}(t, x_i, y_i, z_i)$};

g. edge-smoothing each said windowed, refiltered, shaped, filtered, segmented and detrended unipolar time-and-point-dependent depolarization signal $wrs\,fdsS_{UPi}(t, x_i, y_i, z_i)$, thereby forming a set of edge-smoothed, windowed, refiltered, shaped, filtered, detrended and segmented unipolar time-and-point-dependent depolarization signals {$ewrs\,fdsS_{UPi}(t, x_i, y_i, z_i)$} and, edge-smoothing each said corresponding windowed, refiltered, shaped, filtered, detrended and segmented bipolar time-and-point-dependent depolarization signal $wrs\,fdsS_{BPi}(t, x_i, y_i, z_i)$, thereby forming a set of corresponding edge-smoothed, windowed, refiltered, shaped, filtered, detrended and segmented bipolar time-and-point-dependent depolarization signals {$ewrs\,fdsS_{BPi}(t, x_i, y_i, z_i)$};

h. computing a unipolar point-dependent discrete frequency spectrum $DFS_{UPi}(f, x_i, y_i, z_i)$ for each said edge-smoothed, windowed, refiltered, shaped, filtered, segmented and detrended unipolar time-and-point-dependent depolarization signal $ewrs\,fdsS_{UPi}(t, x_i, y_i, z_i)$, thereby forming a set of unipolar point-dependent discrete frequency spectra $\{DFS_{UPi} (f, x_i, y_i, z_i)\}$; and, computing a corresponding bipolar point-dependent discrete frequency spectrum $DFS_{BPi}(f, x_i, y_i, z_i)$ for each said corresponding edge-smoothed, windowed, refiltered, shaped, filtered, segmented and detrended bipolar time-and-point-dependent depolarization signal $ewrsfdsS_{BPi}(t, x_i, y_i, z_i)$, thereby forming a set of corresponding bipolar point-dependent discrete frequency spectra $\{DFS_{BPi}(f, x_i, y_i, z_i)\}$;

i. computing said unipolar point-dependent discrete power spectrum $DPS_{UPi}(f, x_i, y_i, z_i)$ for each said edge-smoothed, windowed, refiltered, shaped, filtered, segmented and detrended unipolar time-and-point-dependent depolarization signal $ewrsfdsS_{UPi}(t, x_i, y_i, z_i)$, thereby forming said set of unipolar point-dependent discrete power spectra $\{DPS_{UPi}(f, x_i, y_i, z_i)\}$;

j. computing said corresponding bipolar point-dependent discrete power spectrum $DPS_{BPi}(f, x_i, y_i, z_i)$ for each said edge-smoothed, windowed, refiltered, shaped, filtered, segmented and detrended bipolar time-and-point-dependent depolarization signal $ewrsfdsS_{BPi}(t, x_i, y_i, z_i)$, thereby forming said set of corresponding bipolar point-dependent discrete power spectra $\{DPS_{BPi}(f, x_i, y_i, z_i)\}$.

4. The method of claim 3, wherein said step of computing a unipolar point-dependent discrete frequency spectrum comprises computing a Fast Fourier Transform for said edge-smoothed, windowed, refiltered, shaped, filtered, segmented and detrended unipolar time-and-point-dependent depolarization signal $ewrsfdsS_{UPi}(t, x_i, y_i, z_i)$; and said step of computing a bipolar point-dependent discrete frequency spectrum comprises computing a Fast Fourier Transform for said edge-smoothed, windowed, refiltered, shaped, filtered, segmented and detrended bipolar time-and-point-dependent depolarization signal $ewrsfdsS_{BPi}(t, x_i, y_i, z_i)$.

5. The method of claim 3, wherein said first frequency limit $F_{lim1}$ is about 1 Hz and said second frequency limit $F_{lim2}$ is about 30 Hz.

6. The method of claim 3, wherein said third frequency limit $F_{lim3}$ is about 3 Hz and said fourth frequency limit $F_{lim4}$ is about 30 Hz.

7. The method of claim 1, wherein each said point-dependent product dominant frequency $DF_{PRODi}(x_i, y_i, z_i)$ comprises a frequency in each said point-dependent discrete power spectrum product $DPS_{PRODi}(f, x_i, y_i, z_i)$ that is associated with an absolute maximum power density in each said point-dependent discrete power spectrum product $DPS_{PRODi}(f, x_i, y_i, z_i)$.

8. The method of claim 1, wherein said step of computing a point-dependent product dominant frequency $DF_{PRODi}(x_i, y_i, z_i)$ further comprises the step of mapping each point-dependent product dominant frequency $DF_{PRODi}(x_i, y_i, z_i)$ of said set of point-dependent product dominant frequencies $\{DF_{PRODi}(x_i, y_i, z_i)\}$ to said point $P_i(x_i, y_i, z_i)$ of said acquisition set of points $\{P_i(x_i, y_i, z_i)\}$ on or within said heart with which said point-dependent product dominant frequency $DF_{PRODi}(x_i, y_i, z_i)$ is associated.

9. The method of claim 1, wherein said step of assigning the coordinates of said maximum point-dependent product dominant frequency $DF_{MAXPRODi}(x_i, y_i, z_i)$ to said SSFA., further comprises the steps of:

a. computing a point-dependent product regularity index $RI_{PRODi}(x_i, y_i, z_i)$ for each point-dependent discrete product power spectrum $DPS_{PRODi}(f, x_i, y_i, z_i)$ of said set of point-dependent discrete power spectrum products $\{DPS_{PRODi}(f, x_i, y_i, z_i)\}$, thereby forming a set of point-dependent product regularity indices $\{RI_{PRODi}(x_i, y_i, z_i)\}$;

b. verifying said assignment of the coordinates of said maximum point-dependent product dominant frequency $DF_{MAXPRODi}(x_i, y_i, z_i)$ to said SSFA by interpreting the value of its corresponding point-dependent product regularity index.

10. The method of claim 9, wherein said point-dependent product regularity index $RI_{PRODi}(x_i, y_i, z_i)$ comprises a ratio of a power contained in a point-dependent product dominant frequency band $\Delta_{PRODi}DF$ to a total power computed at all frequencies of said point-dependent discrete power spectrum product $DPS_{PRODi}(f, x_i, y_i, z_i)$, said point-dependent product dominant frequency band $\Delta_{PRODi}DF$ being a frequency band centered about a point-dependent product dominant frequency $DF_{PRODi}(x_i, y_i, z_i)$, having a width of about three times a frequency resolution $\Delta f_i$.

11. The method of claim 9, wherein said step of computing a point-dependent product regularity index $RI_{PRODi}(x_i, y_i, z_i)$ further comprises the step of mapping each point-dependent product regularity index $RI_{PRODi}(x_i, y_i, z_i)$ of said set of point-dependent product regularity indices $\{RI_{PRODi}(x_i, y_i, z_i)\}$ to said point $P_i(x_i, y_i, z_i)$ of said acquisition set of points $\{P_i(x_i, y_i, z_i)\}$ on or within said heart with which said product regularity index $RI_{PRODi}(x_i, y_i, z_i)$ is associated.

12. A computer program product, comprising a computer usable medium having a computer readable program code embodied therein, wherein the computer readable program code comprises an algorithm adapted to execute a method of identifying the spatial coordinates of at least one sustaining source of fibrillatory activity ("SSFA") in a heart, said method comprising the steps of:

a. simultaneously acquiring a unipolar time-dependent depolarization signal $S_{UP}(t)$ and a corresponding bipolar time-dependent depolarization signal $S_{BP}(t)$ from each acquisition point $P_i(x_i, y_i, z_i)$ of an acquisition set of points $\{P_i(x_i, y_i, z_i)\}$ on or within said heart, each said acquisition point $P_i(x_i, y_i, z_i)$ having unique spatial coordinates $(x_i, y_i, z_i)$ identified from a pre-stored set of cardiac points $\{cP_i(x_i, y_i, z_i)\}$;

b. forming a set of unipolar time-and-point-dependent depolarization signals $\{S_{UPi}(t, x_i, y_i, z_i)\}$ by assigning to each said unipolar time-dependent depolarization signal $S_{UP}(t)$ the spatial coordinates $(x_i, y_i, z_i)$ of the acquisition point $P_i(x_i, y_i, z_i)$ from which it was acquired; and, forming a set of corresponding bipolar time-and-point-dependent depolarization signals $\{S_{BPi}(t, x_i, y_i, z_i)\}$ by assigning to each said corresponding bipolar time-dependent depolarization signal $S_{BP}(t)$ the spatial coordinates $(x_i, y_i, z_i)$ of the acquisition point $P_i(x_i, y_i, z_i)$ from which it was simultaneously acquired;

c. forming a set of unipolar point-dependent discrete power spectra $\{DPS_{UPi}(f, x_i, y_i, z_i)\}$ by computing a unipolar point-dependent discrete power spectrum $DPS_{UPi}(f, x_i, y_i, z_i)$ for each said unipolar time-and-point-dependent depolarization signal $\{S_{UPi}(t, x_i, y_i, z_i)\}$; and, forming a set of bipolar point-dependent discrete power spectra $\{DPS_{BPi}(f, x_i, y_i, z_i)\}$ by computing a bipolar point-dependent discrete power spectrum $DPS_{BPi}(f, x_i, y_i, z_i)$ for each said corresponding bipolar time-and-point-dependent depolarization signal $\{S_{BPi}(t, x_i, y_i, z_i)\}$;

d. forming a set of point-dependent discrete power spectrum products $\{DPS_{PRODi}(f, x_i, y_i, z_i)\}$ by multiplying each said unipolar point-dependent discrete power spectrum $DPS_{UPi}(f, x_i, y_i, z_i)$ of said set of unipolar point-dependent discrete power spectra $\{DPS_{UPi}(f, x_i, y_i, z_i)\}$ by each said corresponding bipolar point-dependent discrete power spectrum $DPS_{BPi}(f, x_i, y_i, z_i)$ of said set of corresponding bipolar point-dependent discrete power spectra $\{DPS_{BPi}(f, x_i, y_i, z_i)\}$;

e. computing a point-dependent product dominant frequency $DF_{PRODi}(x_i, y_i, z_i)$ for each point-dependent discrete product power spectrum $DPS_{PRODi}(f, x_i, y_i, z_i)$ of said set of point-dependent discrete power spectrum products $\{DPS_{PRODi}(f, x_i, y_i, z_i)\}$, thereby forming a set of point-dependent product dominant frequencies $\{DF_{PRODi}(x_i, y_i, z_i)\}$;

f. selecting a maximum point-dependent product dominant frequency $DF_{MAXPRODi}(x_i, y_i, z_i)$ from said set of point-dependent product dominant frequencies $\{DF_{PRODi}(x_i, y_i, z_i)\}$;

g. assigning the coordinates of said maximum point-dependent product dominant frequency $DF_{MAXPRODi}(x_i, y_i, z_i)$ to said at least one SSFA.

13. The computer program product of claim 12, wherein said unique spatial coordinates $(x_i, y_i, z_i)$ of each said acquisition point $P_i(x_i, y_i, z_i)$ are determined by:

a. defining a spatial coordinate system (x, y, z) for the identification of cardiac points $cP_i(x_i, y_i, z_i)$ having spatial coordinates $(x_i, y_i, z_i)$ on or within said heart;

b. storing said cardiac points $cP_i(x_i, y_i, z_i)$ on a computer recordable medium as a set cardiac points $\{cP_i(x_i, y_i, z_i)\}$;

c. assigning to each acquisition point $P_i(x_i, y_i, z_i)$ the coordinates of the cardiac point with which it is spatially coincident.

14. The computer program product of claim 12, further comprising during execution of the step of forming a set of unipolar time-and-point-dependent depolarization signals $\{S_{UPi}(t, x_i, y_i, z_i)\}$ and forming a set of corresponding bipolar time-and-point-dependent depolarization signals $\{S_{BPi}(t, x_i, y_i, z_i)\}$:

a. storing said set of unipolar time-and-point-dependent depolarization signals $\{S_{UPi}(t, x_i, y_i, z_i)\}$ on a computer recordable medium; and, b. storing said set of bipolar time-and-point-dependent depolarization signals $\{S_{BPi}(t, x_i, y_i, z_i)\}$ on a computer recordable medium.

15. The computer program product of claim 14, wherein said first frequency limit $F_{lim1}$ is about 1 Hz and said second frequency limit $F_{lim2}$ is about 30 Hz.

16. The computer program product of claim 14, wherein said third frequency limit $F_{lim3}$ is about 3 Hz and said fourth frequency limit $F_{lim4}$ is about 30 Hz.

17. The computer program product of claim 12, further comprising during execution of the step of computing a unipolar point-dependent discrete power spectrum $DPS_{UPi}(f, x_i, y_i, z_i)$ for each said unipolar time-and-point-dependent depolarization signal $\{S_{UPi}(t, x_i, y_i, z_i)\}$ and computing a bipolar point-dependent discrete power spectrum $DPS_{BPi}(f, x_i, y_i, z_i)$ for each said corresponding bipolar time-and-point-dependent depolarization signal $\{S_{BPi}(t, x_i, y_i, z_i)\}$:

a. selecting a predefined segment of each said unipolar time-and-point-dependent depolarization signal $S_{UPi}(t, x_i, y_i, z_i)$, thereby forming a set of segmented unipolar time and-point-dependent depolarization signals $\{sS_{UPi}(t, x_i, y_i, z_i)\}$; and, selecting a predefined segment of each of said corresponding bipolar time-and-point-dependent depolarization signal $S_{BPi}(t, x_i, y_i, z_i)$, thereby forming a set of corresponding segmented bipolar time-and-point-dependent depolarization signals $\{sS_{BPi}(t, x_i, y_i, z_i)\}$;

b. detrending each said segmented unipolar time-and-point-dependent depolarization signal $sS_{UPi}(t, x_i, y_i, z_i)$, thereby forming a set of detrended and segmented unipolar time-and-point-dependent depolarization signals $\{dsS_{UPi}(t, x_i, y_i, z_i)\}$; and, detrending each said corresponding segmented bipolar time-and-point-dependent depolarization signal $sS_{BPi}(t, x_i, y_i, z_i)$, thereby forming a set of corresponding detrended and segmented bipolar time and-point-dependent depolarization signals $\{dsS_{BPi}(t, x_i, y_i, z_i)\}$;

c. band pass filtering each said detrended and segmented unipolar time-and-point-dependent depolarization signal $dsS_{UPi}(t, x_i, y_i, z_i)$ between a first frequency limit $F_{lim1}$ and a second frequency limit $F_{lim2}$, thereby forming a set of filtered, detrended and segmented unipolar time and-point-dependent depolarization signals $\{fdsS_{UPi}(t, x_i, y_i, z_i)\}$; and, band pass filtering each said corresponding detrended and segmented bipolar time-and-point-dependent depolarization signal $dsS_{BPi}(t, x_i, y_i, z_i)$ between said first frequency limit $F_{lim1}$ and said second frequency limit $F_{lim2}$, thereby forming a set of corresponding filtered, detrended and segmented bipolar time-and-point-dependent depolarization signals $\{fdsS_{BPi}(t, x_i, y_i, z_i)\}$;

d. convolving each said filtered, segmented and detrended unipolar time-and-point-dependent depolarization signal $fdsS_{UPi}(t, x_i, y_i, z_i)$ with a shaping signal $s(t)$, thereby forming a set of shaped, filtered, detrended and segmented unipolar time-and-point-dependent depolarization signals $\{s fdsS_{UPi}(t, x_i, y_i, z_i)\}$; and, convolving each said corresponding filtered, detrended and segmented bipolar time-and-point-dependent depolarization signal $fdsS_{BPi}(t, x_i, y_i, z_i)$ with said shaping signal $s(t)$, thereby forming a set of corresponding shaped, filtered, detrended and segmented bipolar time-and-point-dependent depolarization signals $\{s fdsS_{BPi}(t, x_i, y_i, z_i)\}$;

e. band pass filtering each said shaped, filtered, segmented and detrended unipolar time-and-point-dependent depolarization signal $s fdsS_{UPi}(t, x_i, y_i, z_i)$ between a third frequency limit $F_{lim3}$ and a fourth frequency limit $F_{lim4}$, thereby forming a set of refiltered, shaped, filtered, detrended and segmented unipolar time-and-point-dependent depolarization signals $\{rs fdsS_{UPi}(t, x_i, y_i, z_i)\}$; and, band pass filtering each said shaped, filtered, detrended and segmented bipolar time-and-point-dependent depolarization signal $s fdsS_{BPi}(t, x_i, y_i, z_i)$ between said third frequency limit $F_{lim3}$ and said fourth frequency limit $F_{lim4}$, thereby forming a set of corresponding refiltered, shaped, filtered, detrended and segmented bipolar time-and-point-dependent depolarization signals $\{rs fdsS_{BPi}(t, x_i, y_i, z_i)\}$;

f. windowing each said refiltered, shaped, filtered, detrended and segmented unipolar time-and-point-dependent depolarization signal $rs fdsS_{UPi}(t, x_i, y_i, z_i)$, thereby forming a set of windowed, refiltered, shaped, filtered, detrended and segmented unipolar time-and-point-dependent depolarization signals $\{wrs fdsS_{UPi}(t, x_i, y_i, z_i)\}$ and, windowing each said corresponding refiltered, shaped, filtered, detrended and segmented bipolar time-and-point-dependent depolarization signal $rs fdsS_{BPi}(t, x_i, y_i, z_i)$, thereby forming a set of corresponding windowed, refiltered, shaped, filtered, detrended and segmented bipolar time-and-point-dependent depolarization signals $\{wrs fdsS_{BPi}(t, x_i, y_i, z_i)\}$;

g. edge-smoothing each said windowed, refiltered, shaped, filtered, segmented and detrended unipolar time-and-point-dependent depolarization signal $wrsfdsS_{UPi}$ (t, $x_i$, $y_i$, $z_i$), thereby forming a set of edge-smoothed, windowed, refiltered, shaped, filtered, detrended and segmented unipolar time-and-point-dependent depolarization signals {$ewrsfdss_{UPi}$ (t, $x_i$, $y_i$, $z_i$)} and, edge-smoothing each said corresponding windowed, refiltered, shaped, filtered, detrended and segmented bipolar time-and-point-dependent depolarization signal $wrsfdsS_{BPi}$ (t, $x_i$, $y_i$, $z_i$), thereby forming a set of corresponding edge-smoothed, windowed, refiltered, shaped, filtered, detrended and segmented bipolar time-and-point-dependent depolarization signals {$ewrsfdsS_{BPi}$ (t, $x_i$, $y_i$, $z_i$)};

h. computing a unipolar point-dependent discrete frequency spectrum for each said edge-smoothed, windowed, refiltered, shaped, filtered, segmented and detrended unipolar time-and-point-dependent depolarization signal $ewrsfdsS_{UPi}$ (t, $x_i$, $y_i$, $z_i$), thereby forming a set of unipolar point-dependent discrete frequency spectra {$DFS_{UPi}$ (f, $x_i$, $y_i$, $z_i$)}; and, computing a bipolar point-dependent discrete frequency spectrum for each said edge-smoothed, windowed, refiltered, shaped, filtered, segmented and detrended bipolar time-and-point-dependent depolarization signal $ewrsfdsS_{BPi}$ (t, $x_i$, $y_i$, $z_i$), thereby forming said set of bipolar point-dependent discrete frequency spectra {$DFS_{BPi}$ (f, $x_i$, $y_i$, $z_i$)};

i. computing said unipolar point-dependent discrete power spectrum for each said edge-smoothed, windowed, refiltered, shaped, filtered, segmented and detrended unipolar time-and-point-dependent depolarization signal $ewrsfdsS_{UPi}$ (t, $x_i$, $y_i$, $z_i$), thereby forming said set of unipolar point-dependent discrete power spectra {$DPS_{UPi}$ (f, $x_i$, $y_i$, $z_i$)};

j. computing a bipolar point-dependent discrete power spectrum for each said edge-smoothed, windowed, refiltered, shaped, filtered, segmented and detrended bipolar time-and-point-dependent depolarization signal $ewrsfdsS_{BPi}$ (t, $x_i$, $y_i$, $z_i$), thereby forming said set of bipolar point-dependent discrete power spectra {$DPS_{BPi}$ (f, $x_i$, $y_i$, $z_i$)}.

18. The computer program product of claim 17, further comprising during execution of the step of forming said set of segmented unipolar time and-point-dependent depolarization signals {$sS_{UPi}$ (t, $x_i$, $y_i$, $z_i$)}; and, forming said set of corresponding segmented bipolar time-and-point-dependent depolarization signals {$sS_{BPi}$ (t, $x_i$, $y_i$, $z_i$)}:

a. storing said set of segmented unipolar time and-point-dependent depolarization signals {$sS_{UPi}$ (t, $x_i$, $y_i$, $z_i$)} on a computer recordable medium; and, b. storing said set of corresponding segmented bipolar time and-point-dependent depolarization signals {$sS_{BPi}$ (t, $x_i$, $y_i$, $z_i$)} on a computer recordable medium.

19. The computer program product of claim 17, further comprising during execution of the step of forming said set of detrended and segmented unipolar time-and-point-dependent depolarization signals {$dsS_{UPi}$ (t, $x_i$, $y_i$, $z_i$)} and forming said set of corresponding detrended and segmented bipolar time and-point-dependent depolarization signals {$dsS_{BPi}$ (t, $x_i$, $y_i$, $z_i$)}:

a. storing said set of detrended and segmented unipolar time-and-point-dependent depolarization signals {$dsS_{UPi}$ (t, $x_i$, $y_i$, $z_i$)} on a computer recordable medium; and, b. storing said set of corresponding detrended and segmented bipolar time and-point-dependent depolarization signals {$dsS_{BPi}$ (t, $x_i$, $y_i$, $z_i$)} on a computer recordable medium.

20. The computer program product of claim 17, further comprising during execution of the step of forming said set of filtered, detrended and segmented unipolar time-and-point-dependent depolarization signals {$fdsS_{UPi}$ (t, $x_i$, $y_i$, $z_i$)} and forming said set of corresponding filtered, detrended and segmented bipolar time and-point-dependent depolarization signals {$fdsS_{BPi}$ (t, $x_i$, $y_i$, $z_i$)} further comprises the steps of:

a. storing said set of filtered, detrended and segmented unipolar time-and-point-dependent depolarization signals {$fdsS_{UPi}$ (t, $x_i$, $y_i$, $z_i$)} on a computer recordable medium; and, b. storing said set of corresponding filtered, detrended and segmented bipolar time and-point-dependent depolarization signals {$fdsS_{BPi}$ (t, $x_i$, $y_i$, $z_i$)} on a computer recordable medium.

21. The computer program product of claim 17, further comprising during execution of the step of forming said set of shaped filtered, detrended and segmented unipolar time-and-point-dependent depolarization signals {$sfdsS_{UPi}$ (t, $x_i$, $y_i$, $z_i$)} and forming said set of corresponding shaped, filtered, detrended and segmented bipolar time and-point-dependent depolarization signals {$sfdsS_{BPi}$ (t, $x_i$, $y_i$, $z_i$)}:

a. storing said set of shaped, filtered, detrended and segmented unipolar time-and-point-dependent depolarization signals {$sfdsS_{UPi}$ (t, $x_i$, $y_i$, $z_i$)} on a computer recordable medium; and, b. storing said set of corresponding shaped, filtered, detrended and segmented bipolar time and-point-dependent depolarization signals {$sfdsS_{BPi}$ (t, $x_i$, $y_i$, $z_i$)} on a computer recordable medium.

22. The computer program product of claim 17, further comprising during execution of the step 23. The computer program product of claim 17, further comprising during execution of the step of forming said set of windowed, refiltered, shaped, filtered, detrended and segmented unipolar time-and-point-dependent depolarization signals {$wrsfdsS_{UPi}$ (t, $x_i$, $y_i$, $z_i$)} and forming said set of corresponding windowed, refiltered, shaped, filtered, detrended and segmented bipolar time and-point-dependent depolarization signals {$wrsfdsS_{BPi}$ (t, $x_i$, $y_i$, $z_i$)}:

a. storing said set of windowed, refiltered, shaped, filtered, detrended and segmented unipolar time-and-point-dependent depolarization signals {$wrsfdsS_{UPi}$ (t, $x_i$, $y_i$, $z_i$)} on a computer recordable medium; and, b. storing said set of corresponding windowed, refiltered, shaped, filtered, detrended and segmented bipolar time and-point-dependent depolarization signals {$rsfdsS_{BPi}$ (t, $x_i$, $y_i$, $z_i$)} on a computer recordable medium.

24. The computer program product of claim 17, further comprising during execution of the step of forming said set of edge-smoothed, windowed, refiltered, shaped, filtered, detrended and segmented unipolar time-and-point-dependent depolarization signals {$ewrsfdsS_{UPi}$ (t, $x_i$, $y_i$, $z_i$)} and forming said set of corresponding edge-smoothed, windowed, refiltered, shaped, filtered, detrended and segmented bipolar time and-point-dependent depolarization signals {$ewrsfdsS_{BPi}$ (t, $x_i$, $y_i$, $z_i$)}:

a. storing said set of edge-smoothed, windowed, refiltered, shaped, filtered, detrended and segmented unipolar time-and-point-dependent depolarization signals {$ewrsfdsS_{UPi}$ (t, $x_i$, $y_i$, $z_i$)} on a computer recordable medium; and, b. storing said set of corresponding edge-smoothed, windowed, refiltered, shaped, filtered, detrended and segmented bipolar time and-point-dependent depolarization signals $\{ewrsfdsS_{BPi}(t, x_i, y_i, z_i)\}$ on a computer recordable medium.

25. The computer program product of claim 17, further comprising during execution of the step of computing a unipolar point-dependent discrete frequency spectrum comprises computing a Fast Fourier Transform for said edge-smoothed, windowed, refiltered, shaped, filtered, segmented and detrended unipolar time-and-point-dependent depolarization signal $ewrsfdsS_{UPi}(t, x_i, y_i, z_i)$; and said step of computing a bipolar point-dependent discrete frequency spectrum comprises computing a Fast Fourier Transform for said edge-smoothed, windowed, refiltered, shaped, filtered, segmented and detrended bipolar time-and-point-dependent depolarization signal $ewrsfdsS_{BPi}(t, x_i, y_i, z_i)$.

26. The computer program product of claim 17, further comprising during execution of the step of forming said set of unipolar point-dependent discrete frequency spectra $\{DFS_{UPi}(f, x_i, y_i, z_i)\}$ and forming said set of bipolar point-dependent discrete frequency spectra $\{DFS_{BPi}(f, x_i, y_i, z_i)\}$:
   a. storing said set of unipolar point-dependent discrete frequency spectra $\{DFS_{UPi}(f, x_i, y_i, z_i)\}$ on a computer recordable medium; and,
   b. storing said set of bipolar point-dependent discrete frequency spectra $\{DFS_{BPi}(f, x_i, y_i, z_i)\}$ on a computer recordable medium.

27. The computer program product of claim 17, further comprising during execution of the step of forming said set of unipolar point-dependent discrete power spectra $\{DPS_{UPi}(f, x_i, y_i, z_i)\}$ and forming said set of bipolar point-dependent discrete power spectra $\{DPS_{BPi}(f, x_i, y_i, z_i)\}$:
   a. storing said set of unipolar point-dependent discrete power spectra $\{DPS_{UPi}(f, x_i, y_i, z_i)\}$ on a computer recordable medium; and,
   b. storing said set of bipolar point-dependent discrete power spectra $\{DPS_{BPi}(f, x_i, y_i, z_i)\}$ on a computer recordable medium.

28. The computer program product of claim 17, further comprising during execution of the step of forming said set of point-dependent discrete power spectrum products $\{DPS_{PRODi}(f, x_i, y_i, z_i)\}$, storing said set of point-dependent discrete power spectrum products $\{DPS_{PRODi}(f, x_i, y_i, z_i)\}$ on a computer recordable medium.

29. The computer program product of claim 17, further comprising during execution of the step of forming said set of point-dependent product dominant frequencies $\{DF_{PRODi}(x_i, y_i, z_i)\}$, storing said set of point-dependent product dominant frequencies $\{DF_{PRODi}(x_i, y_i, z_i)\}$ on a computer recordable medium.

30. The computer program product of claim 12, wherein each said point-dependent product dominant frequency $DF_{PRODi}(x_i, y_i, z_i)$ comprises a frequency in each said point-dependent discrete power spectrum product $DPS_{PRODi}(f, x_i, y_i, z_i)$ that is associated with an absolute maximum power density in each said point-dependent discrete power spectrum product $DPS_{PRODi}(f, x_i, y_i, z_i)$.

31. The computer program product of claim 12, further comprising during execution of the step of computing a point-dependent product dominant frequency $DF_{PRODi}(x_i, y_i, z_i)$, mapping each point-dependent product dominant frequency $DF_{PRODi}(x_i, y_i, z_i)$ of said set of point-dependent product dominant frequencies $\{DF_{PRODi}(x_i, y_i, z_i)\}$ to said acquisition point $P_i(x_i, y_i, z_i)$ of said acquisition set of points $\{P_i(x_i, y_i, z_i)\}$ with which said point-dependent product dominant frequency $DF_{PRODi}(x_i, y_i, z_i)$ is associated.

32. The computer program product of claim 12, further comprising during execution of the step of assigning the coordinates of said maximum point-dependent product dominant frequency $DF_{MAXPRODi}(x_i, y_i, z_i)$ to said SSFA:
   a. computing a point-dependent product regularity index $RI_{PRODi}(x_i, y_i, z_i)$ for each point-dependent discrete product power spectrum $DPS_{PRODi}(f, x_i, y_i, z_i)$ of said set of point-dependent discrete power spectrum products $\{DPS_{PRODi}(f, x_i, y_i, z_i)\}$, thereby forming a set of point-dependent product regularity indices $\{RI_{PRODi}(x_i, y_i, z_i)\}$;
   b. verifying said assignment of the coordinates of said maximum point-dependent product dominant frequency $DF_{MAXPRODi}(x_i, y_i, z_i)$ to said SSFA by interpreting the value of its corresponding point-dependent product regularity index.

33. The computer program product of claim 32, wherein said point-dependent product regularity index $RI_{PRODi}(x_i, y_i, z_i)$ comprises a ratio of a power contained in a point-dependent product dominant frequency band $\Delta_{PRODi}DF$ to a total power computed at all frequencies of said point-dependent discrete power spectrum product $DPS_{PRODi}(f, x_i, y_i, z_i)$, said point-dependent product dominant frequency band $\Delta_{PRODi}DF$ being a frequency band centered about a point-dependent product dominant frequency $DF_{PRODi}(x_i, y_i, z_i)$, having a width of about three times a frequency resolution $\Delta f_i$.

34. The computer program product of claim 32, further comprising during execution of the step of computing a point-dependent product regularity index $RI_{PRODi}(x_i, y_i, z_i)$, mapping each point-dependent product regularity index $RI_{PRODi}(x_i, y_i, z_i)$ of said set of point-dependent product regularity indices $\{RI_{PRODi}(x_i, y_i, z_i)\}$ to said acquisition point $P_i(x_i, y_i, z_i)$ of said acquisition set of points $\{P_i(x_i, y_i, z_i)\}$ with which said product regularity index $RI_{PRODi}(x_i, y_i, z_i)$ is associated.

* * * * *